United States Patent [19]

Tohda et al.

[11] Patent Number: 6,130,070
[45] Date of Patent: Oct. 10, 2000

[54] **INDUCTION PROMOTER GENE AND SECRETORY SIGNAL GENE USABLE IN *SCHIZOSACCHAROMYCES POMBE*, EXPRESSION VECTORS HAVING THE SAME, AND USE THEREOF**

[75] Inventors: Hideki Tohda; Yuko Hama; Hiromichi Kumagai, all of Yokohama, Japan

[73] Assignee: Asahi Glass Company Ltd., Tokyo, Japan

[21] Appl. No.: 09/331,581

[22] PCT Filed: Oct. 30, 1998

[86] PCT No.: PCT/JP98/04929

§ 371 Date: Jun. 30, 1999

§ 102(e) Date: Jun. 30, 1999

[87] PCT Pub. No.: WO99/23223

PCT Pub. Date: May 14, 1999

[30] Foreign Application Priority Data

Oct. 31, 1997 [JP] Japan .................................. 9-314608

[51] Int. Cl.[7] .......................... C12P 21/06; C07H 21/00; C12N 1/19; C12N 15/52; C12N 15/63
[52] U.S. Cl. ................. 435/69.1; 435/254.2; 435/320.1; 536/23.1; 536/23.74; 536/24.1
[58] Field of Search .................... 536/24.1, 23.1, 536/23.74; 435/320.1, 254.2, 69.1

[56] References Cited

U.S. PATENT DOCUMENTS 5,817,478 10/1998 Tohda et al. .
5,919,654 7/1999 Hama et al. .

OTHER PUBLICATIONS

N. Tanaka et al., "Isolation and Characterization of an Invertase and its Repressor Genes from Schizosaccharomyces Pombe", Biochem. Biophys. Res. Commun. vol. 245, pp. 246–253, Apr. 1998.

S. Moreno et al., "Purification and Characterization of the Invertase from Schizosaccharomyces", Biochem. J., vol. 267, pp. 697–702, 1990.

S. Yoshioka et al., "Identification of Open Reading Frames in Schizosaccharomyces Pombe cDNAS", DNA Res., vol. 4, pp. 363–369, Dec. 1997.

J.A. Perez et al., "Cloning and Sequence Analysis of the Invertase Gene INV1 from the Yeast Pichia Anomala", Curr. Genet., vol. 29, pp. 234–240, 1996.

L. Salokin et al., "Short Repeated Elements in the Upstream Regulatory Region of the SUC2 Gene of Saccharomyces Cerevisiae", Mol. Cell. Biol., vol. 6, pp. 2324–2333, 1986.

*Primary Examiner*—Terry Mckelvey
*Attorney, Agent, or Firm*—Oblon, Spivak, McClelland, Maier & Neustadt, P.C.

[57] ABSTRACT

An isolated DNA in an invertase gene from *Schizosaccharomyces pombe*, which is located in a region involved in catabolite repression. The DNA may be incorporated into cloning vector, particularly a vector containing a heterologous protein structural gene. The vector can be used to transform *Schizosaccharomyces pombe*. A heterologous protein may be produced by incubating the transformant and isolating the protein.

12 Claims, 15 Drawing Sheets

```
S. pombe inv1        51 : TTAPNGTCLGNYNEYLPSGYYNATDRPKIHFTPSSGFMNDPNGLVY--TG
S. occidentalis      11 : PLTTTFFGYVASSSIDLSVDTSEYNRPLIHFTPEKGWMNDPNGTFYDKTA
S. cerevisiae SUC2    3 : LQAFTFTLAGFAAKMSASMTNETSDRPLVHFTPNKGWMNDPNGLWYDEKD
                              **  ****  *  ******  *

S. pombe inv1       101 : GVYHMFFQYSPKTLTAGE-VHWGHTVSKDLIHWENYPIAIYPDEHENGVL
S. occidentalis      61 : KTWHLYFQYNPNATAWGQPLYWGHATSNDLVHWDEHEMAIGPEHDNEGIF
S. cerevisiae SUC2   53 : AKWHTYFQYNPNDTVWGTPLFWGHATSDDLTNWEDQPIAIAPKRNDSG--
                           * ** *       *    ***  *  *  *

S. pombe inv1       151 : SLPFSGSAVVDVHN-----SSGLFSNDTI-PEERIVLIYTDHWTGVAERQ
S. occidentalis     111 : ----SGSIVVDHNN-----TSGFF-NSSIDPNQRIVAIYTNNMPDL-QTQ
S. cerevisiae SUC2  103 : --AFSGSMVVDYNN-----TSGFF-NDTIDPRQRCVAIWT-YNTPESEEQ
                             *** * * **     ** *   *      * ****         *

S. pombe inv1       201 : AIAYTTDGGYTFKKYSGNPVLDINSLQFRDPKVMWDFDANRWVIIVAMSQ
S. occidentalis     161 : DIAFSLDGGYTFTKYENNPVIDVSSNQFRDPKVFWHERFKSMDHGCSEIA
S. cerevisiae SUC2  153 : YISYSTDGGYTFTEYQKNPVLAANSTQFRDPKVFWYEPSQKWIMTAAKSQ
                            *   *** **  *      *    *******  *

S. pombe inv1       251 : NYGIAFYSSYDLIHWTELSVFSTSGYLGLQYECPGMARVPVEGTDEYK-W
S. occidentalis     211 : RVKIQIFGSANLKNWVLNSNFS-SGYYGNQYGMSRLIEVPIENSDKSK-W
S. cerevisiae SUC2  203 : DYKIEIYSSDDLKSWKTESAFANEGFLGYQYECPGLIEVPTEQDPSKSYW
                            *   *  *   *      *   *  *  **      **         *

S. pombe inv1       301 : VLFISINPGAP-LGGSVVQYFVGDWNGTNFVPDDGQTRFVDLGKDFYA-S
S. occidentalis     261 : VMFLAINPGSP-LGGSINQYFVGDFDGFQFVPDDSQTRFVDIGKDFYA-F
S. cerevisiae SUC2  253 : VMFISINPGAP-AGGSFNQYFVGSFNGTHFEAFDNQSRVVDFGKDYYALQ
                           *  ****   *** *** *   *   *     *    *  * ***  **

S. pombe inv1       351 : ALYHSSSANADVIGVGWASNWQYTNQAPTQVF-RSAMTVARKFTLRDVPQ
S. occidentalis     311 : QTF--SEVEHGVLGLAWASNWQYADQVPTNPW-RSSTSLARNYTLRYVMQ
S. cerevisiae SUC2  303 : TFFNTDPTYGSALGIAWASNWEYSAFVPTNPW-RSSMSLVRKFSLNTEYQ
                                ****     *    * *  *    *  * I  *
```

FIG. 1

CBB stain

Western blot

SEQUENCE LISTING

<160> NUMBER OF SEQ ID NOS: 24

<210> SEQ ID NO 1
<211> LENGTH: 4748
<212> TYPE: DNA
<213> ORGANISM: Schizosaccharomyces pombe
<220> FEATURE:
<221> NAME/KEY: CDS
<222> LOCATION: (2810)..(4552)

<400> SEQUENCE: 1

```
ggatcctagt ccgcgaaatc gagatgcttt gaagattaaa attaaattta attttatgcg      60
agactggttt ccttattttt tgtatagtcg catgcaagcg aggttcgcat aatttggaaa     120 ataaggtag tcaagaagac gttgaattaa ggctgcagtt tcaaagtact ctacaaacga     180
ttccttttaa aaaaaaagat tcaaaaaaaa ggcaaagggt ttaagtaatg cttgttattt     240
caatttacct ccaaacagtt actaatgcaa ttgcaaaaaa aaaacctacc tattgaatca     300
aaatttctag cccatccatc gctcctcaag ataaaggaat cgatattttg agtttaaggg     360
agttgctgat agatttcaga attaaaaatt tttggaaaag gatgtcgaga acaagaagat     420
acgtctagat tgctgatgat gcattctagc agacggaaat acaacgatat gtggacagca     480 cgactttga tccgttcgga tcaaaaggaa gagaaatatc catctttcaa gaagaatgca     540
ggaaaagcaa taaatgccca tttgattcct aaattatccc caaaaatgaa cattatgaga     600
tcttcttgtg ggagacagga aatttcgcaa ttccaaacga aaattcggct ctttttttta     660
ccccacagtt gcggggtaaa tgatgtaacg gaccttgggg gaaaggatga tgagttagtt     720
gggaagcgga aaaaatggaa aacggaagta agaatagaaa ccagtatggc tgagtgcaat     780
ggcggaaaag attttacaga gatgacaaga atctatttat ctataaggaa aaactttttc     840
```

```
caaatttgtc taaaaacgca ttctcctcaa ttgcctctag gtagatgata taacgaattg      900
gaacgagaca tcgctaaccg gttttctttg taaatgacat tttgtagtgg gagtaagttt      960
gaatggaggg atagacagat gaatagtatg agatagaaga atagtatata taatgattaa     1020
gatgaacaaa taaaaattga agaaaaaaag aaattgttgg ctcatttggt tcatacacat     1080
gttggttcat acaactttta cccatcgtaa gtattataag taaaaaatag agtacgaaaa     1140
gctataagta gtgaagcaaa aaatagaaa atagaaaaa aaatatata taaaaaata        1200 taataaaaat aaaactcata agagacgtaa aacacaagaa ttgtctatca tttgttcttt     1260
aagaagcacc accattctgt aaaactcttc atttctcatt agcaaggacc cttttcattc     1320
cttcctcttt agaatccttt tcattataac gaattggata atacgcaaat aagaacacat     1380
cccctaaata cgatatatcg atccatttt tactttgcct agcttattgc tgtacaattc     1440
catttaaata gtttctcctc aagaaagatc gtcaatggag gcgacaatat accggaattt     1500
aagttgcgga cacagagctt gaaaagactg catttgtat tgttttcaag taaatgaaac      1560
tgagttttga agtctcaaaa tacatcttat gtattgaaca ttagaagaac atataagata     1620
gatcttgaga gctcaattca tcgacattct agccatcata ctgcgatctt agacattgtc     1680
agcacaacct tagatcgaaa atgaacacgt taccaaacgt tgtctaaaac ttgccgaatc     1740
ttatctccgc attacttccg taatccttag tacatacgct gcaatttcgg aaggtcatga     1800 tcgactttt gtgtagctat aagtgacgca aatgagaaac atgacaaggt gcgatattta      1860
gcaagatatt atgcatttga tggagaaagg aaatttcgga tgtatatata gtaccgttag     1920
ctgcgctttt tttggtcatc cataattttc aaactcactg ctttcgatca gatttaccgt     1980
ttttaaggtc tttattgctt tgtgatctgt aggttggaac atctatagtt cattttctaa     2040
aagatccttt catcgtttca tcggatagta atcgttcaag aaaaaaaaag aaaaaaagaa     2100
aaagaaaaag aaaagaaaaa taaccgcta taattcatta cctatttgac tgaaggttct      2160
tcatcttgaa ttgttttgaa tcaaaataaa gaaattatta ttattatttt ttttcttcgc     2220
tttttcttta tccattcgtc gaaactattt ttctgctgat aaaagcaatc attccttttt     2280
cctgcttctc ttgttattcg aatttt aaac gactttttt cctcgtccat tccctaattc     2340
tttgcgacct tttctgattc tatccttggt ttgtactttc gttgtgtaat tgttgagaaa     2400
gtgaactgat tatttaattg ttgtgaaaaa aattctaaaa ctattttgtt tttcttgatc     2460
attcatcctt tgctcgcttg cttgaatatt acagaaattc gtctcccttt caacggaata     2520
tgataatttg ttgaatactc taaatcaatt aacacctatc aaaagctgaa acattaaatc     2580
tattctcacc aaaaaaaaag actcaagctt cttcgttgtt ggccggtctc tttttttgttt    2640 tacgattgtt aaattttata ctcacaactg ccaattctcc acttttgact atttattgat     2700
agtccctatt taatttctg ttcaccgatt atcgtctttt ttgtaaataa tctttcttgg      2760
aaccaaccaa ttaatacgtt ataatcgcta actttgaaga tttgctaca atg ttt ttg     2818
                                                        Met Phe Leu
                                                          1 aaa tat att tta gct agt ggc att tgc ctc gtc tct ctc tta tca tct        2866
Lys Tyr Ile Leu Ala Ser Gly Ile Cys Leu Val Ser Leu Leu Ser Ser
    5                  10                  15 aca aac gcg gct ccc cgt cac tta tat gta aaa cgt tat cct gtc att       2914
Thr Asn Ala Ala Pro Arg His Leu Tyr Val Lys Arg Tyr Pro Val Ile
 20                  25                  30                  35 tat aat gct tcc aac atc act gaa gtc agc aat tct acc acc gtt cct       2962
Tyr Asn Ala Ser Asn Ile Thr Glu Val Ser Asn Ser Thr Thr Val Pro
```

-continued

|  | 40 |  |  |  |  | 45 |  |  |  |  | 50 |  |  |  |  |  |
|---|---|---|---|---|---|---|---|---|---|---|---|---|---|---|---|---|
| cct | cct | cca | ttc | gta | aat | aca | acg | gcc | cct | aat | ggg | act | tgt | ttg | ggt | 3010 |
| Pro | Pro | Pro | Phe | Val | Asn | Thr | Thr | Ala | Pro | Asn | Gly | Thr | Cys | Leu | Gly |  |
|  |  |  | 55 |  |  |  |  | 60 |  |  |  |  | 65 |  |  |  |

| aac | tat | aac | gag | tat | ctt | cct | tca | gga | tat | tac | aat | gct | acc | gat | cgt | 3058 |
|---|---|---|---|---|---|---|---|---|---|---|---|---|---|---|---|---|
| Asn | Tyr | Asn | Glu | Tyr | Leu | Pro | Ser | Gly | Tyr | Tyr | Asn | Ala | Thr | Asp | Arg |  |
|  | 70 |  |  |  |  | 75 |  |  |  |  | 80 |  |  |  |  |  |

| ccc | aaa | att | cat | ttt | act | cct | tct | tcc | ggt | ttc | atg | aat | gat | cca | aac | 3106 |
|---|---|---|---|---|---|---|---|---|---|---|---|---|---|---|---|---|
| Pro | Lys | Ile | His | Phe | Thr | Pro | Ser | Ser | Gly | Phe | Met | Asn | Asp | Pro | Asn |  |
| 85 |  |  |  |  | 90 |  |  |  |  | 95 |  |  |  |  |  |  |

| gga | ttg | gta | tat | act | ggc | ggc | gtc | tat | cac | atg | ttc | ttc | caa | tat | tca | 3154 |
|---|---|---|---|---|---|---|---|---|---|---|---|---|---|---|---|---|
| Gly | Leu | Val | Tyr | Thr | Gly | Gly | Val | Tyr | His | Met | Phe | Phe | Gln | Tyr | Ser |  |
| 100 |  |  |  | 105 |  |  |  |  | 110 |  |  |  |  | 115 |  |  |

| cca | aaa | act | cta | aca | gcc | ggc | gaa | gtt | cat | tgg | ggt | cac | aca | gtt | tcc | 3202 |
|---|---|---|---|---|---|---|---|---|---|---|---|---|---|---|---|---|
| Pro | Lys | Thr | Leu | Thr | Ala | Gly | Glu | Val | His | Trp | Gly | His | Thr | Val | Ser |  |
|  |  |  | 120 |  |  |  |  | 125 |  |  |  |  | 130 |  |  |  |

| aag | gat | tta | atc | cat | tgg | gag | aat | tat | cct | att | gcc | atc | tac | ccc | gat | 3250 |
|---|---|---|---|---|---|---|---|---|---|---|---|---|---|---|---|---|
| Lys | Asp | Leu | Ile | His | Trp | Glu | Asn | Tyr | Pro | Ile | Ala | Ile | Tyr | Pro | Asp |  |
|  |  |  | 135 |  |  |  |  | 140 |  |  |  |  | 145 |  |  |  |

| gaa | cat | gaa | aac | gga | gtt | ttg | tcc | ctc | cca | ttt | agt | ggc | agt | gca | gtc | 3298 |
|---|---|---|---|---|---|---|---|---|---|---|---|---|---|---|---|---|
| Glu | His | Glu | Asn | Gly | Val | Leu | Ser | Leu | Pro | Phe | Ser | Gly | Ser | Ala | Val |  |
|  |  | 150 |  |  |  |  | 155 |  |  |  |  | 160 |  |  |  |  |

| gtc | gat | gtt | cat | aat | tct | tcc | ggt | ctc | ttt | tcc | aac | gac | acc | att | ccg | 3346 |
|---|---|---|---|---|---|---|---|---|---|---|---|---|---|---|---|---|
| Val | Asp | Val | His | Asn | Ser | Ser | Gly | Leu | Phe | Ser | Asn | Asp | Thr | Ile | Pro |  |
| 165 |  |  |  |  | 170 |  |  |  |  | 175 |  |  |  |  |  |  |

| gaa | gag | cgc | att | gtt | tta | att | tat | acc | gat | cat | tgg | act | ggt | gtt | gct | 3394 |
|---|---|---|---|---|---|---|---|---|---|---|---|---|---|---|---|---|
| Glu | Glu | Arg | Ile | Val | Leu | Ile | Tyr | Thr | Asp | His | Trp | Thr | Gly | Val | Ala |  |
| 180 |  |  |  | 185 |  |  |  |  | 190 |  |  |  |  | 195 |  |  |

| gag | cgt | cag | gct | att | gcg | tat | acc | act | gat | ggt | gga | tat | act | ttc | aaa | 3442 |
|---|---|---|---|---|---|---|---|---|---|---|---|---|---|---|---|---|
| Glu | Arg | Gln | Ala | Ile | Ala | Tyr | Thr | Thr | Asp | Gly | Gly | Tyr | Thr | Phe | Lys |  |
|  |  |  | 200 |  |  |  |  | 205 |  |  |  |  | 210 |  |  |  |

| aaa | tat | tca | gga | aat | ccc | gtt | ctt | gac | att | aat | tca | ctt | caa | ttc | cgc | 3490 |
|---|---|---|---|---|---|---|---|---|---|---|---|---|---|---|---|---|
| Lys | Tyr | Ser | Gly | Asn | Pro | Val | Leu | Asp | Ile | Asn | Ser | Leu | Gln | Phe | Arg |  |
|  |  | 215 |  |  |  |  | 220 |  |  |  |  | 225 |  |  |  |  |

| gac | ccc | aag | gta | ata | tgg | gat | ttc | gat | gct | aat | cgt | tgg | gtg | atg | att | 3538 |
|---|---|---|---|---|---|---|---|---|---|---|---|---|---|---|---|---|
| Asp | Pro | Lys | Val | Ile | Trp | Asp | Phe | Asp | Ala | Asn | Arg | Trp | Val | Met | Ile |  |
|  |  | 230 |  |  |  |  | 235 |  |  |  |  | 240 |  |  |  |  |

| gta | gct | atg | tct | caa | aat | tat | gga | att | gcc | ttt | tat | tcc | tcc | tat | gac | 3586 |
|---|---|---|---|---|---|---|---|---|---|---|---|---|---|---|---|---|
| Val | Ala | Met | Ser | Gln | Asn | Tyr | Gly | Ile | Ala | Phe | Tyr | Ser | Ser | Tyr | Asp |  |
|  | 245 |  |  |  |  | 250 |  |  |  |  | 255 |  |  |  |  |  |

| ttg | att | cac | tgg | acc | gag | tta | tct | gtt | ttc | tcc | act | tct | ggt | tat | ttg | 3634 |
|---|---|---|---|---|---|---|---|---|---|---|---|---|---|---|---|---|
| Leu | Ile | His | Trp | Thr | Glu | Leu | Ser | Val | Phe | Ser | Thr | Ser | Gly | Tyr | Leu |  |
| 260 |  |  |  | 265 |  |  |  |  | 270 |  |  |  |  | 275 |  |  |

| ggg | ttg | caa | tat | gaa | tgc | cct | gga | atg | gct | cgt | gtg | ccc | gtt | gaa | ggc | 3682 |
|---|---|---|---|---|---|---|---|---|---|---|---|---|---|---|---|---|
| Gly | Leu | Gln | Tyr | Glu | Cys | Pro | Gly | Met | Ala | Arg | Val | Pro | Val | Glu | Gly |  |
|  |  |  | 280 |  |  |  |  | 285 |  |  |  |  | 290 |  |  |  |

| acc | gat | gaa | tac | aaa | tgg | gta | ctc | ttc | atc | tcc | atc | aat | cct | ggc | gct | 3730 |
|---|---|---|---|---|---|---|---|---|---|---|---|---|---|---|---|---|
| Thr | Asp | Glu | Tyr | Lys | Trp | Val | Leu | Phe | Ile | Ser | Ile | Asn | Pro | Gly | Ala |  |
|  |  | 295 |  |  |  |  | 300 |  |  |  |  | 305 |  |  |  |  |

| cca | ttg | gga | gga | tcc | gtt | gtc | caa | tac | ttt | gtt | ggc | gat | tgg | aat | ggt | 3778 |
|---|---|---|---|---|---|---|---|---|---|---|---|---|---|---|---|---|
| Pro | Leu | Gly | Gly | Ser | Val | Val | Gln | Tyr | Phe | Val | Gly | Asp | Trp | Asn | Gly |  |
|  |  | 310 |  |  |  |  | 315 |  |  |  |  | 320 |  |  |  |  |

| aca | aac | ttc | gtc | ccc | gat | gat | ggc | caa | act | aga | ttc | gta | gac | ttg | ggt | 3826 |
|---|---|---|---|---|---|---|---|---|---|---|---|---|---|---|---|---|
| Thr | Asn | Phe | Val | Pro | Asp | Asp | Gly | Gln | Thr | Arg | Phe | Val | Asp | Leu | Gly |  |
|  | 325 |  |  |  |  | 330 |  |  |  |  | 335 |  |  |  |  |  |

| aag | gac | ttt | tac | gcc | agc | gct | ttg | tat | cac | tcg | tct | tcc | gcc | aat | gcc | 3874 |
|---|---|---|---|---|---|---|---|---|---|---|---|---|---|---|---|---|
| Lys | Asp | Phe | Tyr | Ala | Ser | Ala | Leu | Tyr | His | Ser | Ser | Ser | Ala | Asn | Ala |  |
| 340 |  |  |  |  | 345 |  |  |  |  | 350 |  |  |  |  | 355 |  |

| gat | gtt | att | gga | gtt | gga | tgg | gct | agc | aac | tgg | caa | tac | acc | aac | caa | 3922 |
|---|---|---|---|---|---|---|---|---|---|---|---|---|---|---|---|---|

|     |     |     |     |     |     |     |     |     |     |     |     |      |
| --- | --- | --- | --- | --- | --- | --- | --- | --- | --- | --- | --- | ---- |
| Asp | Val | Ile | Gly | Val | Gly | Trp | Ala | Ser | Asn | Trp | Gln | Tyr Thr Asn Gln |
|     |     |     | 360 |     |     |     |     | 365 |     |     |     | 370 |

```
gct cct act caa gtt ttc cgc agt gct atg aca gtt gca cga aaa ttc      3970
Ala Pro Thr Gln Val Phe Arg Ser Ala Met Thr Val Ala Arg Lys Phe
            375                 380                 385 act ctt cgc gac gtt cct cag aac ccc atg acc aac ctt act tct ctc      4018
Thr Leu Arg Asp Val Pro Gln Asn Pro Met Thr Asn Leu Thr Ser Leu
        390                 395                 400 att caa acc cca ttg aat gtt tct ctc tta cga gat gaa aca cta ttt      4066
Ile Gln Thr Pro Leu Asn Val Ser Leu Leu Arg Asp Glu Thr Leu Phe
    405                 410                 415 acc gca ccc gtt atc aat agt tca agt agt ctt tcg ggc tct ccg att      4114
Thr Ala Pro Val Ile Asn Ser Ser Ser Ser Leu Ser Gly Ser Pro Ile
420                 425                 430                 435 act ctt cca agc aat acc gca ttc gag ttc aat gtc aca ctc agt atc      4162
Thr Leu Pro Ser Asn Thr Ala Phe Glu Phe Asn Val Thr Leu Ser Ile
                440                 445                 450 aat tac aca gaa ggc tgc aca aca gga tat tgt ctg ggg cgt att atc      4210
Asn Tyr Thr Glu Gly Cys Thr Thr Gly Tyr Cys Leu Gly Arg Ile Ile
            455                 460                 465 att gat tct gat gat cca tac aga tta caa tcc atc tcc gtg gac gtt      4258
Ile Asp Ser Asp Asp Pro Tyr Arg Leu Gln Ser Ile Ser Val Asp Val
        470                 475                 480 gat ttt gca gct agc act tta gtc att aat cgt gcc aaa gct cag atg      4306
Asp Phe Ala Ala Ser Thr Leu Val Ile Asn Arg Ala Lys Ala Gln Met
    485                 490                 495 gga tgg ttt aat tca ctt ttc acg cct tct ttt gcc aac gat att tac      4354
Gly Trp Phe Asn Ser Leu Phe Thr Pro Ser Phe Ala Asn Asp Ile Tyr
500                 505                 510                 515 att tat gga aac gta act ttg tat ggt att gtt gac aat gga ttg ctt      4402
Ile Tyr Gly Asn Val Thr Leu Tyr Gly Ile Val Asp Asn Gly Leu Leu
                520                 525                 530 gaa ctg tat gtc aat aat ggc gaa aaa act tac act aat gac ttt ttc      4450
Glu Leu Tyr Val Asn Asn Gly Glu Lys Thr Tyr Thr Asn Asp Phe Phe
            535                 540                 545 ttc ctt caa gga gca aca cct gga cag atc agc ttc gct gct ttc caa      4498
Phe Leu Gln Gly Ala Thr Pro Gly Gln Ile Ser Phe Ala Ala Phe Gln
        550                 555                 560 ggc gtt tct ttc aat aat gtt acc gtt acg cca tta aag act atc tgg      4546
Gly Val Ser Phe Asn Asn Val Thr Val Thr Pro Leu Lys Thr Ile Trp
    565                 570                 575 aat tgc taaatatttt gtttcaagtt aggaaagtat aataactttt gtccctgcat       4602
Asn Cys
580 attcaattgt aaagtttagt ttatcctttc atcgtaacca caattgtcac ctaaatctct    4662 aaaaatctct tcacttatct agttaatgtc gtaacaaaaa agtccagtag cttcgggaaa    4722 tgatgcttgg aatcatacaa gtcgac                                        4748

<210> SEQ ID NO 2
<211> LENGTH: 581
<212> TYPE: PRT
<213> ORGANISM: Schizosaccharomyces pombe

<400> SEQUENCE: 2

Met Phe Leu Lys Tyr Ile Leu Ala Ser Gly Ile Cys Leu Val Ser Leu
 1               5                  10                  15

Leu Ser Ser Thr Asn Ala Ala Pro Arg His Leu Tyr Val Lys Arg Tyr
            20                  25                  30
```

-continued

```
Pro Val Ile Tyr Asn Ala Ser Asn Ile Thr Glu Val Ser Asn Ser Thr
         35                  40                  45

Thr Val Pro Pro Pro Phe Val Asn Thr Thr Ala Pro Asn Gly Thr
 50                  55                  60

Cys Leu Gly Asn Tyr Asn Glu Tyr Leu Pro Ser Gly Tyr Tyr Asn Ala
 65                  70                  75                  80

Thr Asp Arg Pro Lys Ile His Phe Thr Pro Ser Ser Gly Phe Met Asn
                 85                  90                  95

Asp Pro Asn Gly Leu Val Tyr Thr Gly Gly Val Tyr His Met Phe Phe
                100                 105                 110

Gln Tyr Ser Pro Lys Thr Leu Thr Ala Gly Glu Val His Trp Gly His
                115                 120                 125

Thr Val Ser Lys Asp Leu Ile His Trp Glu Asn Tyr Pro Ile Ala Ile
        130                 135                 140

Tyr Pro Asp Glu His Glu Asn Gly Val Leu Ser Leu Pro Phe Ser Gly
145                 150                 155                 160

Ser Ala Val Val Asp Val His Asn Ser Ser Gly Leu Phe Ser Asn Asp
                165                 170                 175

Thr Ile Pro Glu Glu Arg Ile Val Leu Ile Tyr Thr Asp His Trp Thr
                180                 185                 190

Gly Val Ala Glu Arg Gln Ala Ile Ala Tyr Thr Thr Asp Gly Gly Tyr
        195                 200                 205

Thr Phe Lys Lys Tyr Ser Gly Asn Pro Val Leu Asp Ile Asn Ser Leu
210                 215                 220

Gln Phe Arg Asp Pro Lys Val Ile Trp Asp Phe Asp Ala Asn Arg Trp
225                 230                 235                 240

Val Met Ile Val Ala Met Ser Gln Asn Tyr Gly Ile Ala Phe Tyr Ser
                245                 250                 255

Ser Tyr Asp Leu Ile His Trp Thr Glu Leu Ser Val Phe Ser Thr Ser
                260                 265                 270

Gly Tyr Leu Gly Leu Gln Tyr Glu Cys Pro Gly Met Ala Arg Val Pro
        275                 280                 285

Val Glu Gly Thr Asp Glu Tyr Lys Trp Val Leu Phe Ile Ser Ile Asn
290                 295                 300

Pro Gly Ala Pro Leu Gly Gly Ser Val Val Gln Tyr Phe Val Gly Asp
305                 310                 315                 320

Trp Asn Gly Thr Asn Phe Val Pro Asp Asp Gly Gln Thr Arg Phe Val
                325                 330                 335

Asp Leu Gly Lys Asp Phe Tyr Ala Ser Ala Leu Tyr His Ser Ser Ser
                340                 345                 350

Ala Asn Ala Asp Val Ile Gly Val Gly Trp Ala Ser Asn Trp Gln Tyr
        355                 360                 365

Thr Asn Gln Ala Pro Thr Gln Val Phe Arg Ser Ala Met Thr Val Ala
370                 375                 380

Arg Lys Phe Thr Leu Arg Asp Val Pro Gln Asn Pro Met Thr Asn Leu
385                 390                 395                 400

Thr Ser Leu Ile Gln Thr Pro Leu Asn Val Ser Leu Leu Arg Asp Glu
                405                 410                 415

Thr Leu Phe Thr Ala Pro Val Ile Asn Ser Ser Ser Leu Ser Gly
                420                 425                 430

Ser Pro Ile Thr Leu Pro Ser Asn Thr Ala Phe Glu Phe Asn Val Thr
        435                 440                 445

Leu Ser Ile Asn Tyr Thr Glu Gly Cys Thr Thr Gly Tyr Cys Leu Gly
```

```
                450               455               460
        Arg Ile Ile Ile Asp Ser Asp Asp Pro Tyr Arg Leu Gln Ser Ile Ser
        465                 470               475                 480

Val Asp Val Asp Phe Ala Ala Ser Thr Leu Val Ile Asn Arg Ala Lys
                        485               490               495

Ala Gln Met Gly Trp Phe Asn Ser Leu Phe Thr Pro Ser Phe Ala Asn
                    500               505               510

Asp Ile Tyr Ile Tyr Gly Asn Val Thr Leu Tyr Gly Ile Val Asp Asn
                    515               520               525

Gly Leu Leu Glu Leu Tyr Val Asn Asn Gly Glu Lys Thr Tyr Thr Asn
                    530               535               540

Asp Phe Phe Leu Gln Gly Ala Thr Pro Gly Gln Ile Ser Phe Ala
        545                 550               555               560

Ala Phe Gln Gly Val Ser Phe Asn Asn Val Thr Val Thr Pro Leu Lys
                        565               570               575

Thr Ile Trp Asn Cys
                    580

<210> SEQ ID NO 3
<211> LENGTH: 7286
<212> TYPE: DNA
<213> ORGANISM: Artificial Sequence
<220> FEATURE:
<223> OTHER INFORMATION: Description of Artificial Sequence:DNA

<400> SEQUENCE: 3
agcttgaaaa aacctcccac acctccccct gaacctgaaa cataaaatga atgcaattgt      60
tgttgttaac ttgtttattg cagcttataa tggttacaaa taaagcaata gcatcacaaa    120
tttcacaaat aaagcatttt tttcactgca ttctagttgt ggtttgtcca aactcatcaa    180
tgtatcttat catgtctgga tcgatcccgg caggttgggc gtcgcttggt cggtcatttc    240 gaacccaga gtcccgctca aagaactcg tcaagaaggc gatagaaggc gatgcgctgc     300
gaatcgggag cggcgatacc gtaaagcacg aggaagcggt cagcccattc gccgccaagc    360
tcttcagcaa tatcacgggt agccaacgct atgtcctgat agcggtccgc cacacccagc    420
cggccacagt cgatgaatcc agaaaagcgg ccattttcca ccatgatatt cggcaagcag    480
gcatcgccat gggtcacgac gagatcctcg ccgtcgggca tgcgcgcctt gagcctggcg    540
aacagttcgg ctggcgcgag cccctgatgc tcttcgtcca gatcatcctg atcgacaaga    600
ccggcttcca tccgagtacg tgctcgctcg atgcgatgtt tcgcttggtg gtcgaatggg    660
caggtagccg gatcaagcgt atgcagccgc cgcattgcat cagccatgat ggatactttc    720
tcggcaggag caaggtgaga tgacaggaga tcctgccccg gcacttcgcc caatagcagc    780
cagtcccttc ccgcttcagt gacaacgtcg agcacagctg cgcaaggaac gcccgtcgtg    840
gccagccacg atagccgcgc tgcctcgtcc tgcagttcat tcagggcacc ggacaggtcg    900
gtcttgacaa aagaaccgg gcgccctgc gctgacagcc ggaacacggc ggcatcagag    960
cagccgattg tctgttgtgc ccagtcatag ccgaatagcc tctccaccca agcggccgga   1020
gaacctgcgt gcaatccatc ttgttcaatc atgcgaaacg atcctcatcc tgtctcttga   1080
tcagatccgg gacctgaaat aaaagacaaa aagactaaac ttaccagtta actttctggt   1140
ttttcagttc ctcgaggagc tttttgcaaa agcctaggcc tccaaaaaag cctcctcact   1200
acttctggaa tagctcagag gccgaggcgg cctcggcctc tgcataaata aaaaaaatta   1260
gtcagccatg gggcggagaa tgggcggaac tgggcggagt tagggcggg atgggcggag   1320
```

```
ttagggcgg gactatggtt gctgactaat tgagatgcat gctttgcata cttctgcctg    1380
ctggggagcc tggggacttt ccacacctgg ttgctgacta attgagatgc atgctttgca    1440
tacttctgcc tgctggggag cctggggact tccacaccc taactgacac acattccaca    1500
ggacattgat tattgactag ttagtccgcg aaatcgagat gctttgaaga ttaaaattaa    1560
atttaatttt atgcgagact ggtttcctta ttttttgtat agtcgcatgc aagcgaggtt    1620
cgcataattt ggaaaataaa ggtagtcaag aagacgttga attaaggctg cagtttcaaa    1680
gtactctaca aacgattcct tttaaaaaaa aagattcaaa aaaaaggcaa agggtttaag    1740
taatgcttgt tatttcaatt tacctccaaa cagttactaa tgcaattgca aaaaaaaaac    1800
ctacctattg aatcaaaatt tctagcccat ccatcgctcc tcaagataaa ggaatcgata    1860
ttttgagttt aagggagttg ctgatagatt tcagaattaa aaattttttgg aaaaggatgt    1920 cgagaacaag aagatacgtc tagattgctg atgatgcatt ctagcagacg aaatacaac    1980 gatatgtgga cagcacgact tttgatccgt tcggatcaaa aggaagagaa atatccatct    2040
ttcaagaaga atgcaggaaa agcaataaat gcccatttga ttcctaaatt atccccaaaa    2100
atgaacatta tgagatcttc ttgtgggaga caggaaattt cgcaattcca aacgaaaatt    2160
cggctctttt ttttaccccca cagttgcggg gtaaatgatg taacggacct tgggggaaag    2220
gatgatgagt tagttgggaa gcggaaaaaa tggaaaacgg aagtaagaat agaaaccagt    2280
atggctgagt gcaatggcgg aaaagatttt acagagatga caagaatcta tttatctata    2340
aggaaaaact ttttccaaat ttgtctaaaa acgcattctc ctcaattgcc tctaggtaga    2400
tgatataacg aattggaacg agacatcgct aaccggtttt ctttgtaaat gacattttgt    2460
agtgggagta agtttgaatg gagggataga cagatgaata gtatgagata aagaatagt    2520 atatataatg attaagatga acaaataaaa attgaaagaa aaaagaaatt gttggctcat    2580
ttggttcata cacatgttgg ttcatacaac ttttacccat cgtaagtatt ataagtaaaa    2640
aatagagtac gaaaagctat aagtagtgaa gcaaaaaaat agaaaaatag aaaaaaaaat    2700
atatataaaa aaatataata aaaataaaac tcataagaga cgtaaaacac aagaattgtc    2760
tatcatttgt tctttaagaa gcaccaccat tctgtaaaac tcttcatttc tcattagcaa    2820 ggacccttt cattccttcc tctttagaat ccttttcatt ataacgaatt ggataatacg    2880
caaataagaa cacatcccct aaatacgata tatcgatcca tttttactt tgcctagctt    2940 attgctgtac aattccattt aaatagtttc tcctcaagaa agatcgtcaa tggaggcgac    3000
aatataccgg aatttaagtt gcggacacag agcttgaaaa gactgcattt tgtattgttt    3060
tcaagtaaat gaaactgagt tttgaagtct caaaatacat cttatgtatt gaacattaga    3120
agaacatata agatagatct tgagagctca attcatcgac attctagcca tcatactgcg    3180
atcttagaca ttgtcagcac aaccttagat cgaaaatgaa cacgttacca aacgttgtct    3240
aaaacttgcc gaatcttatc tccgcattac ttccgtaatc cttagtacat acgctgcaat    3300
ttcggaaggt catgatcgac tttttgtgta gctataagtg acgcaaatga gaaacatgac    3360
aaggtgcgat atttagcaag atattatgca tttgatggag aaaggaaatt tcggatgtat    3420
atatagtacc gttagctgcg cttttttttgg tcatccataa ttttcaaact cactgctttc    3480
gatcagattt accgttttta aggtctttat tgctttgtga tctgtaggtt ggaacatcta    3540
tagttcattt tctaaaagat cctttcatcg tttcatcgga tagtaatcgt tcaagaaaaa    3600 aaagaaaaa aagaaaaaga aaagaaaag aaaaataaac cgctataatt cattacctat    3660
```

```
ttgactgaag gttcttcatc ttgaattgtt ttgaatcaaa ataaagaaat tattattatt     3720 atttttttc ttcgcttttt ctttatccat tcgtcgaaac tattttttctg ctgataaaag     3780 caatcattcc ttttttcctgc ttctcttgtt attcgaattt taaacgactt tttttcctcg    3840
tccattccct aattctttgc gaccttttct gattctatcc ttggtttgta ctttcgttgt    3900
gtaattgttg agaaagtgaa ctgattattt aattgttgtg aaaaaaattc taaaactatt    3960
ttgtttttct tgatcattca tcctttgctc gcttgcttga atattacaga aattcgtctc    4020
cctttcaacg gaatatgata atttgttgaa tactctaaat caattaacac ctatcaaaag    4080
ctgaaacatt aaatctattc tcaccaaaaa aaaagactca agcttcttcg ttgttggccg    4140
gtctcttttt tgttttacga ttgttaaatt ttatactcac aactgccaat tctccacttt    4200
tgactattta ttgatagtcc ctatttaatt ttctgttcac cgattatcgt cttttttgta    4260 aataatctt cttggaacca accaattaat acgttataat cgctaacttt gaagatttgc     4320
tacaatggca atggtatcag aattcgagct cggtacccgg ggatcctcta gagtcgacct    4380
gcaggcatgc aagcttaaat aggaaagttt cttcaacagg attacagtgt agctacctac    4440
atgctgaaaa atatagcctt taaatcattt ttatattata actctgtata atagagataa    4500
gtccattttt taaaaatgtt ttcccccaaac cataaaaccc tatacaagtt gttctagtaa    4560
caatacatga gaaagatgtc tatgtagctg aaaataaaat gacgtcacaa gacaaaaaaa    4620
aaaaaaaaaa aaaaaaaaaa aaaaaaaaaa aaaaaaaaaa aaaaaaaaaa aaaaaagta    4680 ccttctgagg cggaaagaac cagccggatc cagacatgat aagatacatt gatgagtttg    4740
gacaaaccac aactagaatg cagtgaaaaa aatgctttat ttgtgaaatt tgtgatgcta    4800
ttgctttatt tgtaaccatt ataagctgca ataaacaagt taacaacaac aattgcattc    4860
attttatgtt tcaggttcag ggggaggtgt gggaggtttt ttaaagcaag taaaacctct    4920
acaaatgtgg tatggctgat tatgatccgg ctgcctcgcg cgtttcggtg atgacggtga    4980
aaacctctga cacatgcagc tcccggagac ggtcacagct tgtctgtaag cggatgccgg    5040
gagcagacaa gcccgtcagg gcgcgtcagc gggtgttggc gggtgtcggg gcgcagccat    5100
gacccagtca cgtagcgata gcggagtgta tactggctta actatgcggc atcagagcag    5160
attgtactga gagtgcacca tatgcggtgt gaaataccgc acagatgcgt aaggagaaaa    5220
taccgcatca ggcgctcttc cgcttcctcg ctcactgact cgctgcgctc ggtcgttcgg    5280
ctgcggcgag cggtatcagc tcactcaaag gcggtaatac ggttatccac agaatcaggg    5340
gataacgcag gaaagaatga gcaaaaggcc agcaaaaggc caggaaccgt aaaaaggccg    5400
cgttgctggc gtttttccat aggctccgcc ccctgacga gcatcacaaa aatcgacgct    5460
caagtcagag gtggcgaaac ccgacaggac tataaagata ccaggcgttt ccccctggaa    5520
gctccctcgt gcgctctcct gttccgaccc tgccgcttac cggatacctg tccgcctttc    5580
tcccttcggg aagcgtggcg ctttctcata gctcacgctg taggtatctc agttcggtgt    5640
aggtcgttcg ctccaagctg ggctgtgtgc acgaacccc cgttcagccc gaccgctgcg    5700
ccttatccgg taactatcgt cttgagtcca acccggtaag acacgactta tcgccactgg    5760
cagcagccac tggtaacagg attagcagag cgaggtatgt aggcggtgct acagagttct    5820
tgaagtggtg gcctaactac ggctacacta gaaggacagt atttggtatc tgcgctctgc    5880
tgaagccagt taccttcgga aaagagttg gtagctcttg atccggcaaa caaaccaccg    5940
ctggtagcgg tggttttttt gtttgcaagc agcagattac gcgcagaaaa aaggatctc    6000 aagaagatcc tttgatcttt tctacggggt ctgacgctca gtggaacgaa aactcacgtt    6060
```

-continued

```
aagggatttt ggtcatgaga ttatcaaaaa ggatcttcac ctagatcctt ttaaattaaa      6120
aatgaagttt taaatcaatc taaagtatat atgagtaaac ttggtctgac agttaccaat      6180
gcttaatcag tgaggcacct atctcagcga tctgtctatt tcgttcatcc atagttgcct      6240
gactccccgt cgtgtagata actacgatac gggagggctt accatctggc cccagtgctg      6300
caatgatacc gcgagaccca cgctcaccgg ctccagattt atcagcaata aaccagccag      6360
ccggaagggc cgagcgcaga agtggtcctg caactttatc cgcctccatc cagtctatta      6420
attgttgccg ggaagctaga gtaagtagtt cgccagttaa tagtttgcgc aacgttgttg      6480
ccattgctgc aggcatcgtg gtgtcacgct cgtcgtttgg tatggcttca ttcagctccg      6540
gttcccaacg atcaaggcga gttacatgat cccccatgtt gtgcaaaaaa gcggttagct      6600
ccttcggtcc tccgatcgtt gtcagaagta agttggccgc agtgttatca ctcatggtta      6660
tggcagcact gcataattct cttactgtca tgccatccgt aagatgcttt tctgtgactg      6720
gtgagtactc aaccaagtca ttctgagaat agtgtatgcg cgaccgagt tgctcttgcc       6780 cggcgtcaac acgggataat accgcgccac atagcagaac tttaaaagtg ctcatcattg      6840
gaaaacgttc ttcggggcga aaactctcaa ggatcttacc gctgttgaga tccagttcga      6900 tgtaaccac tcgtgcaccc aactgatctt cagcatcttt tactttcacc agcgtttctg       6960
ggtgagcaaa acaggaagg caaaatgccg caaaaaggg aataagggcg acacggaaat        7020
gttgaatact catactcttc cttttcaat attattgaag catttatcag ggttattgtc       7080
tcatgagcgg atacatattt gaatgtattt agaaaaataa acaaataggg gttccgcgca      7140
catttccccg aaaagtgcca cctgacgtct aagaaaccat tattatcatg acattaacct      7200
ataaaaatag gcgtatcacg aggccctttc gtcttcaaga attggtcgac caattctcat      7260
gtttgacagc ttatcatcga taagct                                          7286
```

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:DNA

<400> SEQUENCE: 4

```
gtttgaattc atgaaygayg gnaaygg                                            27
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:DNA
<220> FEATURE:
<223> OTHER INFORMATION: N is G, C, T, or A

<400> SEQUENCE: 5

```
gtttgaattc yrytggggnc aygc                                               24
```

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:DNA
<220> FEATURE:
<223> OTHER INFORMATION: N is G, C, T, or A -continued

```
<400> SEQUENCE: 6
gtttgaattc acyttnggrt cncgraa                                              27

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:DNA

<400> SEQUENCE: 7
gatgggtaaa actagtatga acca                                                 24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:DNA

<400> SEQUENCE: 8
ttgcgaatta ctagtctccc aca                                                  23

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:DNA

<400> SEQUENCE: 9
gggactagtt agtccgcgaa atcgagatg                                            29

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:DNA

<400> SEQUENCE: 10
gaggaattct gataccattg ccattgtagc aaatcttcaa ag                             42

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:DNA

<400> SEQUENCE: 11
aaagctagcc attgtagcaa atcttcaaag                                           30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:DNA

<400> SEQUENCE: 12
atggctagca agggcgagga gctgttc                                              27

<210> SEQ ID NO 13
<211> LENGTH: 27
```

-continued

```
<212> TYPE: DNA
<213> ORGANISM: Artificial Sequence
<220> FEATURE:
<223> OTHER INFORMATION: Description of Artificial Sequence:DNA

<400> SEQUENCE: 13
cccaagctta cttgtacagc tcgtcca                                      27

<210> SEQ ID NO 14
<211> LENGTH: 7938
<212> TYPE: DNA
<213> ORGANISM: Artificial Sequence
<220> FEATURE:
<223> OTHER INFORMATION: Description of Artificial Sequence:DNA

<400> SEQUENCE: 14
agcttgaaaa aacctcccac acctccccct gaacctgaaa cataaaatga atgcaattgt    60
tgttgttaac ttgtttattg cagcttataa tggttacaaa taaagcaata gcatcacaaa   120
tttcacaaat aaagcatttt tttcactgca ttctagttgt ggtttgtcca aactcatcaa   180
tgtatcttat catgtctgga tcgatcccgg caggttgggc gtcgcttggt cggtcatttc   240 gaacccccaga gtcccgctca aagaactcg tcaagaaggc gatagaaggc gatgcgctgc   300
gaatcgggag cggcgatacc gtaaagcacg aggaagcggt cagcccattc gccgccaagc   360
tcttcagcaa tatcacgggt agccaacgct atgtcctgat agcggtccgc cacacccagc   420
cggccacagt cgatgaatcc agaaaagcgg ccattttcca ccatgatatt cggcaagcag   480
gcatcgccat gggtcacgac gagatcctcg ccgtcgggca tgcgcgcctt gagcctggcg   540
aacagttcgg ctggcgcgag cccctgatgc tcttcgtcca gatcatcctg atcgacaaga   600
ccggcttcca tccgagtacg tgctcgctcg atgcgatgtt tcgcttggtg gtcgaatggg   660
caggtagccg gatcaagcgt atgcagccgc cgcattgcat cagccatgat ggatactttc   720
tcggcaggag caaggtgaga tgacaggaga tcctgccccg gcacttcgcc caatagcagc   780
cagtcccttc ccgcttcagt gacaacgtcg agcacagctg cgcaaggaac gcccgtcgtg   840
gccagccacg atagccgcgc tgcctcgtcc tgcagttcat tcagggcacc ggacaggtcg   900
gtcttgacaa aaagaaccgg gcgcccctgc gctgacagcc ggaacacggc ggcatcagag   960
cagccgattg tctgttgtgc ccagtcatag ccgaatagcc tctccaccca gcggccgga   1020 gaacctgcgt gcaatccatc ttgttcaatc atgcgaaacg atcctcatcc tgtctcttga   1080
tcagatccgg gacctgaaat aaaagacaaa agactaaac ttaccagtta actttctggt   1140
ttttcagttc ctcgaggagc tttttgcaaa agcctaggcc tccaaaaaag cctcctcact   1200
acttctggaa tagctcagag gccgaggcgg cctcggcctc tgcataaata aaaaaatta   1260 gtcagccatg gggcggagaa tgggcggaac tgggcggagt taggggcggg atgggcggag   1320
ttaggggcgg gactatggtt gctgactaat tgagatgcat gctttgcata cttctgcctg   1380
ctggggagcc tggggacttt ccacacctgg ttgctgacta attgagatgc atgctttgca   1440
tacttctgcc tgctggggag cctggggact tccacaccc taactgacac acattccaca   1500
ggacattgat tattgactag ttagtccgcg aaatcgagat gctttgaaga ttaaaattaa   1560
atttaatttt atgcgagact ggtttcctta ttttttgtat agtcgcatgc aagcgaggtt   1620
cgcataattt ggaaaataaa ggtagtcaag aagacgttga attaaggctg cagtttcaaa   1680
gtactctaca aacgattcct tttaaaaaaa agattcaaa aaaaaggcaa agggtttaag   1740
taatgcttgt tatttcaatt tacctccaaa cagttactaa tgcaattgca aaaaaaaac   1800
```

-continued

```
ctacctattg aatcaaaatt tctagcccat ccatcgctcc tcaagataaa ggaatcgata    1860
ttttgagttt aagggagttg ctgatagatt tcagaattaa aaattttttgg aaaaggatgt    1920 cgagaacaag aagatacgtc tagattgctg atgatgcatt ctagcagacg gaaatacaac    1980
gatatgtgga cagcacgact tttgatccgt tcggatcaaa aggaagagaa atatccatct    2040
ttcaagaaga atgcaggaaa agcaataaat gcccatttga ttcctaaatt atccccaaaa    2100
atgaacatta tgagatcttc ttgtgggaga caggaaattt cgcaattcca acgaaaatt     2160 cggctctttt ttttaccccca cagttgcggg gtaaatgatg taacggacct tgggggaaag   2220
gatgatgagt tagttgggaa gcggaaaaaa tggaaaacgg aagtaagaat agaaaccagt    2280
atggctgagt gcaatggcgg aaaagatttt acagagatga caagaatcta tttatctata    2340
aggaaaaact ttttccaaat ttgtctaaaa acgcattctc ctcaattgcc tctaggtaga    2400
tgatataacg aattggaacg agacatcgct aaccggtttt ctttgtaaat gacattttgt    2460
agtgggagta agtttgaatg gagggataga cagatgaata gtatgagata aagaatagt     2520 atatataatg attaagatga acaaataaaa attgaaagaa aaaagaaatt gttggctcat    2580
ttggttcata cacatgttgg ttcatacaac ttttacccat cgtaagtatt ataagtaaaa    2640
aatagagtac gaaaagctat aagtagtgaa gcaaaaaaat agaaaaatag aaaaaaaaat    2700
atatataaaa aaatataata aaaataaaac tcataagaga cgtaaaacac aagaattgtc    2760
tatcatttgt tctttaagaa gcaccaccat tctgtaaaac tcttcatttc tcattagcaa    2820 ggacccttt cattccttcc tctttagaat ccttttcatt ataacgaatt ggataatacg     2880
caaataagaa cacatcccct aaatacgata tatcgatcca ttttttactt tgcctagctt    2940
attgctgtac aattccattt aaatagtttc tcctcaagaa agatcgtcaa tggaggcgac    3000
aatataccgg aatttaagtt gcggacacag agcttgaaaa gactgcattt tgtattgttt    3060
tcaagtaaat gaaactgagt tttgaagtct caaaatacat cttatgtatt gaacattaga    3120
agaacatata agatagatct tgagagctca attcatcgac attctagcca tcatactgcg    3180
atcttagaca ttgtcagcac aaccttagat cgaaaatgaa cacgttacca aacgttgtct    3240
aaaacttgcc gaatcttatc tccgcattac ttccgtaatc cttagtacat acgctgcaat    3300
ttcggaaggt catgatcgac ttttttgtgta gctataagtg acgcaaatga gaaacatgac    3360
aaggtgcgat atttagcaag atattatgca tttgatggag aaaggaaatt tcggatgtat    3420
atatagtacc gttagctgcg cttttttttgg tcatccataa ttttcaaact cactgctttc    3480
gatcagattt accgttttta aggtctttat tgctttgtga tctgtaggtt ggaacatcta    3540
tagttcattt tctaaaagat ccttttcatcg tttcatcgga tagtaatcgt tcaagaaaaa   3600 aaagaaaaa aagaaaaaga aaagaaaag aaaaataaac cgctataatt cattacctat      3660
ttgactgaag gttcttcatc ttgaattgtt ttgaatcaaa ataaagaaat tattattatt    3720
attttttttc ttcgcttttt ctttatccat tcgtcgaaac tattttctg ctgataaaag     3780 caatcattcc ttttttcctgc ttctcttgtt attcgaattt taaacgactt tttttcctcg   3840
tccattccct aattctttgc gacctttttct gattctatcc ttggtttgta ctttcgttgt   3900
gtaattgttg agaaagtgaa ctgattattt aattgttgtg aaaaaaattc taaaactatt    3960 ttgttttttct tgatcattca tcctttgctc gcttgcttga atattacaga aattcgtctc   4020
cctttcaacg gaatatgata atttgttgaa tactctaaat caattaacac ctatcaaaag   4080
ctgaaacatt aaatctattc tcaccaaaaa aaaagactca agcttcttcg ttgttggccg    4140
gtctcttttt tgttttacga ttgttaaatt ttatactcac aactgccaat tctccacttt    4200
```

```
tgactattta ttgatagtcc ctatttaatt ttctgttcac cgattatcgt cttttttgta    4260
aataatcttt cttggaacca accaattaat acgttataat cgctaacttt gaagatttgc    4320
tacaatggct agcaagggcg aggagctgtt caccggggtg gtgcccatcc tggtcgagct    4380
ggacggcgac gtaaacggcc acaagttcag cgtgtccggc gagggcgagg gcgatgccac    4440
ctacggcaag ctgaccctga agttcatctg caccaccggc aagctgcccg tgccctggcc    4500
caccctcgtg accaccctga cctacggcgt gcagtgcttc agccgctacc ccgaccacat    4560
gaagcagcac gacttcttca agtccgccat gcccgaaggc tacgtccagg agcgcaccat    4620
cttcttcaag gacgacggca actacaagac ccgcgccgag gtgaagttcg agggcgacac    4680
cctggtgaac cgcatcgagc tgaagggcat cgacttcaag gaggacggca acatcctggg    4740
gcacaagctg gagtacaact acaacagcca caacgtctat atcatggccg acaagcagaa    4800
gaacggcatc aaggtgaact tcaagatccg ccacaacatc gaggacggca gcgtgcagct    4860
cgccgaccac taccagcaga acacccccat cggcgacggc cccgtgctgc tgcccgacaa    4920
ccactacctg agcacccagt ccgccctgag caaagacccc aacgagaagc gcgatcacat    4980
ggtcctgctg gagttcgtga ccgccgccgg gatcactctc ggcatggacg agctgtacaa    5040
gtaagcttaa ataggaaagt ttcttcaaca ggattacagt gtagctacct acatgctgaa    5100
aaatatagcc tttaaatcat ttttatatta taactctgta taatagagat aagtccattt    5160
tttaaaaatg ttttccccaa accataaaac cctatacaag ttgttctagt aacaatacat    5220
gagaaagatg tctatgtagc tgaaaataaa atgacgtcac aagacaaaaa aaaaaaaaaa    5280
aaaaaaaaaa aaaaaaaaaa aaaaaaaaaa aaaaaaaaaa aaaaaaaaag taccttctga    5340
ggcggaaaga accagccgga tccagacatg ataagataca ttgatgagtt tggacaaacc    5400
acaactagaa tgcagtgaaa aaaatgcttt atttgtgaaa tttgtgatgc tattgcttta    5460
tttgtaacca ttataagctg caataaacaa gttaacaaca acaattgcat tcattttatg    5520
tttcaggttc agggggaggt gtgggaggtt ttttaaagca agtaaaacct ctacaaatgt    5580
ggtatggctg attatgatcc ggctgcctcg cgcgtttcgg tgatgacggt gaaaacctct    5640
gacacatgca gctcccggag acggtcacag cttgtctgta agcggatgcc gggagcagac    5700
aagcccgtca gggcgcgtca gcgggtgttg gcgggtgtcg gggcgcagcc atgacccagt    5760
cacgtagcga tagcggagtg tatactggct taactatgcg gcatcagagc agattgtact    5820
gagagtgcac catatgcggt gtgaaatacc gcacagatgc gtaaggagaa aataccgcat    5880
caggcgctct tccgcttcct cgctcactga ctcgctgcgc tcggtcgttc ggctgcggcg    5940
agcggtatca gctcactcaa aggcggtaat acggttatcc acagaatcag gggataacgc    6000
aggaaagaat gagcaaaagg ccagcaaaag gccaggaacc gtaaaaaggc cgcgttgctg    6060 gcgttttttcc ataggctccg ccccctgac gagcatcaca aaaatcgacg ctcaagtcag    6120
aggtggcgaa acccgacagg actataaaga taccaggcgt ttccccctgg aagctccctc    6180
gtgcgctctc ctgttccgac cctgccgctt accggatacc tgtccgcctt tctcccttcg    6240
ggaagcgtgg cgctttctca tagctcacgc tgtaggtatc tcagttcggt gtaggtcgtt    6300
cgctccaagc tgggctgtgt gcacgaaccc cccgttcagc ccgaccgctg cgccttatcc    6360
ggtaactatc gtcttgagtc aacccggta agacacgact tatcgccact ggcagcagcc    6420
actggtaaca ggattagcag agcgaggtat gtaggcggtg ctacagagtt cttgaagtgg    6480
tggcctaact acggctacac tagaaggaca gtatttggta tctgcgctct gctgaagcca    6540
```

-continued

```
gttaccttcg gaaaaagagt tggtagctct tgatccggca aacaaaccac cgctggtagc    6600
ggtggttttt ttgtttgcaa gcagcagatt acgcgcagaa aaaaggatc tcaagaagat    6660 cctttgatct tttctacggg gtctgacgct cagtggaacg aaaactcacg ttaagggatt    6720
ttggtcatga gattatcaaa aaggatcttc acctagatcc ttttaaatta aaaatgaagt    6780
tttaaatcaa tctaaagtat atatgagtaa acttggtctg acagttacca atgcttaatc    6840
agtgaggcac ctatctcagc gatctgtcta tttcgttcat ccatagttgc ctgactcccc    6900
gtcgtgtaga taactacgat acgggagggc ttaccatctg gccccagtgc tgcaatgata    6960
ccgcgagacc cacgctcacc ggctccagat ttatcagcaa taaaccagcc agccggaagg    7020
gccgagcgca gaagtggtcc tgcaacttta tccgcctcca tccagtctat taattgttgc    7080
cgggaagcta gagtaagtag ttcgccagtt aatagtttgc gcaacgttgt tgccattgct    7140
gcaggcatcg tggtgtcacg ctcgtcgttt ggtatggctt cattcagctc cggttcccaa    7200
cgatcaaggc gagttacatg atcccccatg ttgtgcaaaa aagcggttag ctccttcggt    7260
cctccgatcg ttgtcagaag taagttggcc gcagtgttat cactcatggt tatggcagca    7320
ctgcataatt ctcttactgt catgccatcc gtaagatgct tttctgtgac tggtgagtac    7380
tcaaccaagt cattctgaga atagtgtatg cggcgaccga gttgctcttg cccggcgtca    7440
acacgggata ataccgcgcc acatagcaga actttaaaag tgctcatcat tggaaaacgt    7500 tcttcgggc gaaaactctc aaggatctta ccgctgttga gatccagttc gatgtaaccc    7560
actcgtgcac ccaactgatc ttcagcatct tttactttca ccagcgtttc tgggtgagca    7620
aaaacaggaa ggcaaaatgc cgcaaaaaag ggaataaggg cgacacggaa atgttgaata    7680
ctcatactct tcctttttca atattattga agcatttatc agggttattg tctcatgagc    7740
ggatacatat ttgaatgtat ttagaaaaat aaacaaatag gggttccgcg cacatttccc    7800
cgaaaagtgc cacctgacgt ctaagaaacc attattatca tgacattaac ctataaaaat    7860
aggcgtatca cgaggcccct tcgtcttcaa gaattggtcg accaattctc atgtttgaca    7920
gcttatcatc gataagct                                                 7938
```

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence:DNA

<400> SEQUENCE: 15

```
gggactagtt agtccgcgaa atcgagatg                                       29
```

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence:DNA

<400> SEQUENCE: 16

```
gaggaattct gataccattg ccattgtagc aaatcttcaa ag                        42
```

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence:DNA

<400> SEQUENCE: 17
gggacatgtt tttgaaatat attttagc         28

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:DNA

<400> SEQUENCE: 18
gggaagctta gcaattccag atagtct          27

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:DNA

<400> SEQUENCE: 19
ttgactagtt attaatagta                  20

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence:DNA

<400> SEQUENCE: 20
cccgaattca taacgtttta catataagt         29

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence:DNA

<400> SEQUENCE: 21
aaagaattcc cagtaccccc aacctcttca        30

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:DNA

<400> SEQUENCE: 22
aaaatgattt aaaggctata                   20

<210> SEQ ID NO 23
<211> LENGTH: 332
<212> TYPE: PRT
<213> ORGANISM: Schwanniomyces occidentalis

<400> SEQUENCE: 23

Pro Leu Thr Thr Thr Phe Phe Gly Tyr Val Ala Ser Ser Ser Ile Asp
 1               5                  10                  15

Leu Ser Val Asp Thr Ser Glu Tyr Asn Arg Pro Leu Ile His Phe Thr
            20                  25                  30

Pro Glu Lys Gly Trp Met Asn Asp Pro Asn Gly Thr Phe Tyr Asp Lys
            35                  40                  45

Thr Ala Lys Thr Trp His Leu Tyr Phe Gln Tyr Asn Pro Asn Ala Thr
 50                  55                  60

Ala Trp Gly Gln Pro Leu Tyr Trp Gly His Ala Thr Ser Asn Asp Leu
 65                  70                  75                  80

Val His Trp Asp Glu His Glu Met Ala Ile Gly Pro Glu His Asp Asn
                    85                  90                  95

Glu Gly Ile Phe Ser Gly Ser Ile Val Val Asp His Asn Asn Thr Ser
                100                 105                 110

Gly Phe Phe Asn Ser Ser Ile Asp Pro Asn Gln Arg Ile Val Ala Ile
            115                 120                 125

Tyr Thr Asn Asn Met Pro Asp Leu Gln Thr Gln Asp Ile Ala Phe Ser
130                 135                 140

Leu Asp Gly Gly Tyr Thr Phe Thr Lys Tyr Glu Asn Asn Pro Val Ile
145                 150                 155                 160

Asp Val Ser Ser Asn Gln Phe Arg Asp Pro Lys Val Phe Trp His Glu
                165                 170                 175

Arg Phe Lys Ser Met Asp His Gly Cys Ser Glu Ile Ala Arg Val Lys
                180                 185                 190

Ile Gln Ile Phe Gly Ser Ala Asn Leu Lys Asn Trp Val Leu Asn Ser
            195                 200                 205

Asn Phe Ser Ser Gly Tyr Tyr Gly Asn Gln Tyr Gly Met Ser Arg Leu
            210                 215                 220

Ile Glu Val Pro Ile Glu Asn Ser Asp Lys Ser Lys Trp Val Met Phe
225                 230                 235                 240

Leu Ala Ile Asn Pro Gly Ser Pro Leu Gly Gly Ser Ile Asn Gln Tyr
                245                 250                 255

Phe Val Gly Asp Phe Asp Gly Phe Gln Phe Val Pro Asp Ser Gln
                260                 265                 270

Thr Arg Phe Val Asp Ile Gly Lys Asp Phe Tyr Ala Phe Gln Thr Phe
            275                 280                 285

Ser Glu Val Glu His Gly Val Leu Gly Leu Ala Trp Ala Ser Asn Trp
290                 295                 300

Gln Tyr Ala Asp Gln Val Pro Thr Asn Pro Trp Arg Ser Ser Thr Ser
305                 310                 315                 320

Leu Ala Arg Asn Tyr Thr Leu Arg Tyr Val Met Gln
                325                 330

<210> SEQ ID NO 24
<211> LENGTH: 337
<212> TYPE: PRT
<213> ORGANISM: Saccharomyces cerevisiae

<400> SEQUENCE: 24

Leu Gln Ala Phe Thr Phe Thr Leu Ala Gly Phe Ala Ala Lys Met Ser
 1               5                  10                  15

Ala Ser Met Thr Asn Glu Thr Ser Asp Arg Pro Leu Val His Phe Thr
                20                  25                  30

Pro Asn Lys Gly Trp Met Asn Asp Pro Asn Gly Leu Trp Tyr Asp Glu
            35                  40                  45

Lys Asp Ala Lys Trp His Thr Tyr Phe Gln Tyr Asn Pro Asn Asp Thr
 50                  55                  60

Val Trp Gly Thr Pro Leu Phe Trp Gly His Ala Thr Ser Asp Asp Leu
 65                  70                  75                  80

-continued

```
Thr Asn Trp Glu Asp Gln Pro Ile Ala Ile Ala Pro Lys Arg Asn Asp
             85                  90                  95

Ser Gly Ala Phe Ser Gly Ser Met Val Val Asp Tyr Asn Asn Thr Ser
            100                 105                 110

Gly Phe Phe Asn Asp Thr Ile Asp Pro Arg Gln Arg Cys Val Ala Ile
        115                 120                 125

Trp Thr Tyr Asn Thr Pro Glu Ser Glu Glu Gln Tyr Ile Ser Tyr Ser
    130                 135                 140

Thr Asp Gly Gly Tyr Thr Phe Thr Glu Tyr Gln Lys Asn Pro Val Leu
145                 150                 155                 160

Ala Ala Asn Ser Thr Gln Phe Arg Asp Pro Lys Val Phe Trp Tyr Glu
                165                 170                 175

Pro Ser Gln Lys Trp Ile Met Thr Ala Ala Lys Ser Gln Asp Tyr Lys
                180                 185                 190

Ile Glu Ile Tyr Ser Ser Asp Asp Leu Lys Ser Trp Lys Thr Glu Ser
            195                 200                 205

Ala Phe Ala Asn Glu Gly Phe Leu Gly Tyr Gln Tyr Glu Cys Pro Gly
        210                 215                 220

Leu Ile Glu Val Pro Thr Glu Gln Asp Pro Ser Lys Ser Tyr Trp Val
225                 230                 235                 240

Met Phe Ile Ser Ile Asn Pro Gly Ala Pro Ala Gly Gly Ser Phe Asn
                245                 250                 255

Gln Tyr Phe Val Gly Ser Phe Asn Gly Thr His Phe Glu Ala Phe Asp
                260                 265                 270

Asn Gln Ser Arg Val Val Asp Phe Gly Lys Asp Tyr Tyr Ala Leu Gln
            275                 280                 285

Thr Phe Phe Asn Thr Asp Pro Thr Tyr Gly Ser Ala Leu Gly Ile Ala
        290                 295                 300

Trp Ala Ser Asn Trp Glu Tyr Ser Ala Phe Val Pro Thr Asn Pro Trp
305                 310                 315                 320

Arg Ser Ser Met Ser Leu Val Arg Lys Phe Ser Leu Asn Thr Glu Tyr
                325                 330                 335

Gln
```

INDUCTION PROMOTER GENE AND SECRETORY SIGNAL GENE USABLE IN *SCHIZOSACCHAROMYCES POMBE*, EXPRESSION VECTORS HAVING THE SAME, AND USE THEREOF

This application is a National Stage of International Application PCT/JP98/04929, filed Oct. 30, 1998.

TECHNICAL FIELD

The present invention relates to an inducible promoter gene and secretion signal gene for use in the fission yeast *Schizosaccharomyces pombe* (hereinafter referred to as *S. pombe*), an expression vector containing them and a process for producing a protein using them. In particular, it relates to a process for producing a desired protein wherein the *S. pombe* invertase promoter is used to make it possible to control the timing of the protein production by the presence or absence of a specific nutrient through regulated gene expression, and a process for secretory production of a desired protein by using the secretion signal gene for the *S. pombe* invertase precursor.

BACKGROUND ART

*S. pombe*, despite being a eukaryote, has been studied extensively for its high versatility in genetics, molecular biology and cellular biology as a unicellular organism (Nasim A. et al. eds., Molecular biology of the fission yeast, Academic Press, 1989). In its cultures, monosaccharides such as glucose and fructose are used as the main carbon sources. It is known that in a culture medium lacking these monosaccharides, expression of invertase, the enzyme that degrades sucrose into glucose and fructose, is induced to secure the carbon source necessary for its growth (Moreno S. et al., Arch Microbial. 142, 370, 1985).

*S. pombe* invertase is and is a high-molecular weight glycoprotein located on the cell surface with a molecular weight of about 205000, 67% of which is attributed to sugar chains composed of equimolar amounts of mannose and galactose residues. Molecular weight and amino acid studies of the protein moiety of the pure enzyme and experiments using antibodies have shown high similarlity between *S. pombe* invertase and the invertase from the budding yeast *Saccharomyces cerevisiae* from the viewpoint of protein chemistry (Moreno S. et al., Biochem. J. 267, 697, 1990). It is also known that a drop in glucose concentration de-represses synthesis of invertase (Mitchinson J. et al., Cell Sci 5, 373, 1969).

Induced invertase synthesis (de-repression) is also observed in *Saccharomyces cerevisiae*. Previous detailed studies on genetic regulation of invertase expression, the biosynthetic pathway and the structure of the sugar chain moiety have shown that *Saccharomyces cerevisiae* invertase is encoded by six overlapping genes, SUC1 to SUC5 and SUC7, on one chromosome and that activation of at least one of these SUC genes leads to utilization of sucrose and raffinose (Hohmann S. et al., Curr Genet 11, 217, 1986).

In contrast, with respect to *S. pombe*, although purification of the invertase protein has been reported (Moreno S. et al., 1985), no invertase genes had been identified until the present inventors and coworkers recently reported two overlapping invertase genes $inv0^+$ and $inv1^+$ in *S. pombe*. Because $inv0^+$ is likely a pseudogene having an incomplete open reading frame, $inv1^+$ is the only one gene encoding *S. pombe* invertase, which is supposed to confer the ability to grow on sucrose even in the absence of other carbon sources ("Kobogaku" edited by Yositaka Hashitani, Iwanami Shoten, 1967).

Analysis of the promoter region of the isolated gene suggested that a specific sequence between the 1st and 62nd base pairs is involved catabolite repression.

In *Saccharomyces cerevisiae*, the SUC2 gene is transcribed into two messenger RNAs (mRNAs) from different transcription initiation sites. The shorter one is a constitutive mRNA encoding the intracellular invertase, while the longer one is a mRNA encoding the catabolite-repressible secretory invertase with a de-repression ratio of not less than 200 (Carlson M. et al., Mol. Cell. Biol. 3, 439, 1983). Analysis of the promoter region for the longer mRNA suggested that the transcription initiation factor binds to a specific repeated sequence between positions −650 and −418 (Salokin L et al., Mol. Cell. Biol. 6, 2314, 1986). The region between positions −418 and −140 has been shown to be necessary for glucose repression.

These regions in the SUC2 gene showed no significant homology with the $inv1^+$ upstream region between positions 1 and 2809. However, multiple copies of a so-called 7-bp motif with the sequence (A/C)(A/G)GAAAT, which is repeated at five sites in the region indispensable for glucose derepression, have been found in the $inv1^+$ upstream region. Further, while palindrome stem-loops have been identified at almost the same positions in the upstream regions of glucose-repressible genes (SUC, MAL and GAL), palindrome sequences have also been found in the upstream region of the $inv1^+$ gene from *S. pombe*. These sequences are anticipated to play an important role in glucose repression in *S. pombe*.

The yeast *S. pombe* is phylogenetically different from *Saccharomyces cerevisiae*. It is quite different from other yeasts in the chromosome structure and various mechanisms for genome replication, RNA splicing, transcription and posttranslational modification, and rather resembles animal cells in some of these aspects. For this reason, *S. pombe* is widely used as a eukaryotic model (Giga-Hama and Kumagai, eds., Foreign gene expression in fission yeast *Schizosaccharomyces pombe*, Springer-Verlag, 1997).

*S. pombe* is also widely used as a host for expression of heterologous protein genes and known to be suited especially for expression of genes from animals including human (JP-A-5-15380 and JP-A-7-163373). For its advanced membrane structures including the Goldi body and the endoplasmic reticulum, *S. pombe* is also used for expression of membrane proteins and shows high level expression. For *S. pombe*, constitutive expression vectors (pEVP11, pART1 and pTL2M) and an inducible expression vector using the promoter region of the $nmt1^+$ gene (pREP1) are usually used as expression vectors. No *S. pombe* expression vectors of the GAL type or the SUC type have been known though these types of vectors are commonly used for *Saccharomyces cerevisiae*.

The expression of the SUC2 gene from *Saccharomyces cerevisiae* in *S. pombe* has been shown to be constitutive, not catabolite repressible, though the expression product contains galactose residues conferred by the host (Zarate, V. et al., J Applied Bacteriology, 80, 45, 1996), suggesting differences between *S. pombe* and *Saccharomyces cerevisiae* in the mechanism for catabolite repression of invertase. The differences are of great significance because the promoter from *Saccharomyces cerevisiae* usually used by those skilled in the art for construction of inducible expression vectors of the invertase type (the SUC2 type) is not applicable to *S. pombe* vectors. Therefore, development of *S. pombe* vectors of this type has been long delayed.

On the other hand, the present inventors constructed an expression vector using the secretion signal gene encoding the secretion signal in the precursor of a *S. pombe* mating pheromone (WO96/23890). However, this secretion signal gene is not an all-purpose secretion signal gene, and other secretion signal genes that function in *S. pombe* are desired for production of some types of protein.

DISCLOSURE OF THE INVENTION

As a result of their extensive research with a view to solving the above problems, the present inventors have accomplished the present invention by preparing a new clone of the *S. pombe* invertase gene and constructing an inducible expression vector. They have also found that the N-terminal 22 amino acid sequence in the amino acid of the invertase precursor functions as a secretion signal. On the basis of these findings, they have constructed an expression vector using the secretion signal gene and established secretory production of desired proteins.

The present invention relates to a region in the invertase gene from *S. pombe*, which is involved in catabolite repression, an inducible expression vector using the region and a system using it for heterologous gene expression and provides:

a DNA in an invertase gene from *Schizosaccharomyces pombe*, which is located in a region involved in catabolite repression, a DNA having the base sequence of bases 1 to 2809 in SEQ ID NO: 1 in the Sequence Listing, a recombinant vector containing the sequence of the DNA, a multicloning vector containing the sequence of the DNA and a multicloning site, a multicloning vector having the structure shown in FIG. 9, an expression vector for transformation of *Schizosaccharomyces pombe* containing the sequence of the DNA and a heterologous protein structural gene, a transformant from *Schizosaccharomyces pombe* containing the expression vector, and a process for producing a protein which comprises incubating the transformant and recovering an expressed heterologous protein.

Firstly, the present inventors cloned and sequenced a *S. pombe* invertase gene, which had not been genetically identified. Then, they demonstrated by gene disruption analysis that the invertase gene is responsible for the overall invertase activity. Further, they identified the region involved in catabolite repression and constructed an inducible expression vector using the region. They actually constructed a recombinant vector carrying the gene of a green fluorescent protein, transformed *S. pombe* with the vector and confirmed the expression of the protein by assay of invertase activity and immunological analysis. They also demonstrated repression of the heterologous gene expression in the presence of glucose in the culture medium and derepression by exhaustion of glucose.

The present inventors used the following procedure to identify and characterize the gene of the *S. pombe* invertase precursor:

(1) PCR using a cDNA library from *S. pombe* as a template and primers based on conserved amino acid sequences in invertase genes from many other organisms;

(2) screening of a genomic library from *S. pombe* by plaque hybridization using the PCR product as a probe for positive clones;

(3) confirmation of the positive clones by restriction digestion followed by electrophoresis;

(4) Southern hybridization analysis and total sequencing of a fragment with a specific length in the positive clones;

(5) gene disruption analysis of invertase activity;

(6) investigation of the optimum pH for expression of the invertase gene from *S. pombe* and the effects of the glucose concentration on glucose repression and derepression; and (7) identification of a region indispensable for glucose repression through subcloning of the related upstream region.

Also, the present inventors constructed a *S. pombe* invertase inducible expression vector by the following procedure and actually demonstrated inducible expression of a green fluorescent protein:

(1) construction of an inducible multicloning expression vector pRI0M containing an invertase promoter by modifying a *S. pombe* multicloning vector, pTL2M (JP-A-7-163373);

(2) construction of an inducible expression vector pRI0EGFP for expression of a green fluorescent protein variant from the inducible multicloning vector, pRI0M;

(3) transformation of a wild-type *S. pombe* strain with the inducible expression vector, pRI0EGFP, for expression of the green fluorescent protein variant;

(4) demonstration of the expression of the green fluorescent protein variant by activity (fluorescence) analysis and SDS-PAGE-western blotting; and (5) establishment of the conditions for the inducible expression on the basis of the dependence of the expression level on the glucose concentration in the culture medium.

SEQ ID NO: 1 in the Sequence Listing is the base sequence of the gene of the invertase precursor, which contains a region involved in catabolite repression. The region involved in catabolite repression is the DNA sequence between positions 1 to 2809 of SEQ ID NO: 1 or within the DNA sequence. In the DNA sequence between positions 1 and 2809 of SEQ ID NO: 1, the region extending from position 1 to position 620 of SEQ ID NO: 1 and the region extending from position 1610 to position 2610 of SEQ ID NO: 1 are especially important, as is evident from the results of the analysis in Example 6 shown in FIG. 8 (position 2810 in SEQ ID NO: 1 corresponds to position 1 in FIG. 8). This means that the inducible promoter in the present invention is not restricted to a DNA having the base sequence from position 1 to position 2809 of SEQ ID NO: 1 so long as it contains these genes involved in catabolite repression and functions as an inducible promoter. Still, a DNA having a base sequence from position 1 to position 2809 of SEQ ID NO: 1 is preferable as an inducible promoter because it actually functions in *S. pombe*.

The above-mentioned DNA which contains genes involved in catabolite repression and function as an inducible promoter, preferably having the base sequence from position 1 to position 2809 of SEQ ID NO: 1, is hereinafter referred to as the inducible promoter gene. The inducible promoter gene can be integrated with a vector for construction of recombinant vectors such as multicloning vectors and expression vectors. A multicloning vector is a vector having a multicloning site and provides an expression vector through introduction of a desired structural gene into the multicloning site. An expression vector is a vector containing a structural gene and used for expression of a structural gene encoding a heterologous protein. A "heterologous" protein is a protein which is not inherent in the host. For example, when the host is *S. pombe*, a heterologous protein is a protein which is not inherent in *S. pombe* (such as a human protein).

In the expression vector, the inducible promoter gene is located upstream from the heterologous protein structural gene and regulates expression of the structural gene. The inducible promoter gene in the expression vector regulates the expression of the heterologous protein structural gene downstream, like the inducible promoter gene, located upstream in the base sequence represented by SEQ ID NO: 1 regulates the expression of the structural gene of the invertase precursor. In the multicloning vector, the inducible promoter gene is located upstream from the multicloning site into which a heterologous protein structural gene is to be introduced.

One example of the multicloning vector of the present invention is the multiclonig vector pRI0M constructed in Example 9 and has the structure shown in FIG. 9. The entire base sequence of pRI0M is SEQ ID NO: 3. Inv1-P is the above-mentioned inducible promoter gene, and MCS is the multicloning site. One example of the expression vector of the present invention is the inducible expression vector pRI0EGFP for expression of a green fluorescent protein variant constructed in Example by introducing the structural gene (EGFP-ORF) of a green fluorescent protein variant and has the structure shown in FIG. 10. The entire base sequence of the expression vector pRI0EGFP is SEQ ID NO: 14.

The most suitable cell (host) to transform with the expression vector of the present invention is S. pombe because the inducible promoter gene in the present invention is an inducible promoter gene from S. pombe.

Under catabolite repressing conditions (for example, in a culture medium containing a high level of glucose), S. pombe transformed with the expression vector of the present invention grows with no (or low) expression of the heterologous protein. Growth at this stage without the burden of heterologous protein expression is more efficient than growth under the burden. Subsequent incubation under catabolite derepressing conditions (for example, in a culture medium containing no or a low level of glucose) invites the increased number of S. pombe cells to high level expression of the heterologous protein, though growth of S. pombe is less efficient than under catabolite repressing conditions. Thus, controlled transition between growth of S. pombe and heterologous protein expression through catabolite repression allows more efficient production of a heterologous protein.

Catabolite repression can be controlled not only in an active way as described above but also in a passive way. For example, when a S. pombe transformant is incubated in a culture medium containing a given amount of glucose, the S. pombe grows under catabolite repressing conditions containing a high level of glucose in the initial stage, but later on production of a heterologous protein predominates due to catabolite derepression as glucose is exhausted. This way, more efficient heterologous protein production of than ever is possible without active control of the glucose level.

In addition to the above-mentioned total sequencing of the invertase precursor gene from S. pombe, the present inventors determined the complete amino acid sequence of the invertase precursor (the amino acid sequence in SEQ ID NO: 2). Then, they have found that the first 22 amino acid peptide in the amino acid sequence of the invertase precursor (Met Phe Leu Lys Tyr Ile Leu Ala Ser Gly Ile Cys Leu Val Ser Leu Leu Ser Ser Thr Asn Ala) (amino acids 1–22 of SEQ ID NO: 2) acts as a secretion signal. Hereinafter, the peptide is referred to as the secretion signal.

It is expected that a desired heterologous protein produced in transformed S. pombe cells as a protein fusion having the secretion signal at the N-terminal is secreted from the cells after intracellular processing which splits the protein fusion into the secretion signal and the heterologous protein. The present inventors constructed an expression vector carrying a heterologous protein structural gene (specifically, human interleukin 6-a'c1 variant) fused with a DNA encoding the secretion signal (namely, a structural gene of a protein fusion as mentioned above) and demonstrated secretion of the heterologous protein from S. pombe cells transformed with the expression vector.

The present invention provides the secretion signal, a DNA encoding the secretion signal (hereinafter referred to as a secretion signal gene), a recombinant vector carrying the secretion signal gene, a multicloning vector carrying the secretion signal gene, an expression vector carrying the secretion signal gene and a heterologous protein structural gene for transformation of S. pombe, a S. pombe transformant carrying the expression vector and a process for producing a protein which comprises incubating the transformant and recovering the expressed heterologous protein.

The secretion signal gene is not restricted to the 66-bp sequence extending from position 2810 to position 2875 in SEQ ID NO: 1 and may be a DNA having a different base sequence encoding the amino acid sequence of the secretion signal. In the expression vector, the secretion signal and the heterologous protein structural gene is preferably linked directly. But they may be linked via another DNA sequence, for example, extending from position 2876 in SEQ ID NO: 1. In this case, the protein product has extra amino acid residues at the N-terminal of the heterologous protein but can be converted into the desired heterologous protein by trimming off the N-terminal extra amino acid residues. However, the disadvantage from the presence of these extra amino acid residues usually becomes more serious for the desired protein as the number of extra amino acid residues increases. Therefore, as the intervening DNA between the secretion signal gene and the heterologous protein structural gene, a short DNA encoding at most 10 amino acid residues is preferable. Particular preferably, the secretion signal gene and the heterologous protein structural gene are linked directly.

Construction of an expression vector carrying the secretion signal gene using a multicloning vector can be attained by inserting a heterologous protein structural gene fused with the secretion signal gene into the multicloning site of a multicloning vector or by inserting a heterologous protein structural gene into the multicloning site of a multicloning vector carrying the secretion signal gene. The latter method tends to restrict the structure of the multicloning site because the secretion signal gene is preferred to be located immediately in front of the multicloning site as described above. Therefore, the former method is preferred for construction of an expression vector. As a S. pombe multicloning vector, for example, pTL2M, which is disclosed in JP-A-163373, is preferable.

According to the present invention, an expression vector can be constructed by using both the inducible promoter gene and the secretion signal gene. For example, an expression vector which contains the DNA sequence of from position 1 to position 2875 in SEQ ID No: 1 and a heterologous protein structural gene introduced downstream of the DNA sequence can be constructed. Such an expression vector enables catabolite repressible secretory production of a heterologous protein by the host cell. A similar expression vector can be constructed by using a known secretion signal gene (such as the secretion signal gene disclosed in WO96/23890) instead of the above-mentioned secretion signal gene.

BRIEF DESCRIPTION OF DRAWINGS

The following drawings are presented in connection with the section of Best Mode for Carrying Out the Invention.

FIG. 1 shows a comparison of (partial) amino acid sequences deduced from inv1* (amino acids 58–393 of SEQ ID NO: 2), the *Schwanniomyces occidentalis* invertase gene (SEQ ID NO: 23) and the fission yeast SUC2 gene (SEQ ID NO: 24).

FIG. 4(a) is a photograph of colony gel overlay assay of invertase activity (for phenotype characterization) as a substitute for a drawing. FIG. 4(b) is a schematic explanation of experimental design of the invertase activity assay shown in FIG. 4(a).

FIG. 5(a) is a photograph of colony gel overlay assay of invertase activity (for phenotype characterization) as a substitute for a drawing. FIG. 5(b) is a schematic explanation of experimental design of the invertase activity assay shown in FIG. 5(a).

BEST MODE FOR CARRYING OUT THE INVENTION

Figure 2:
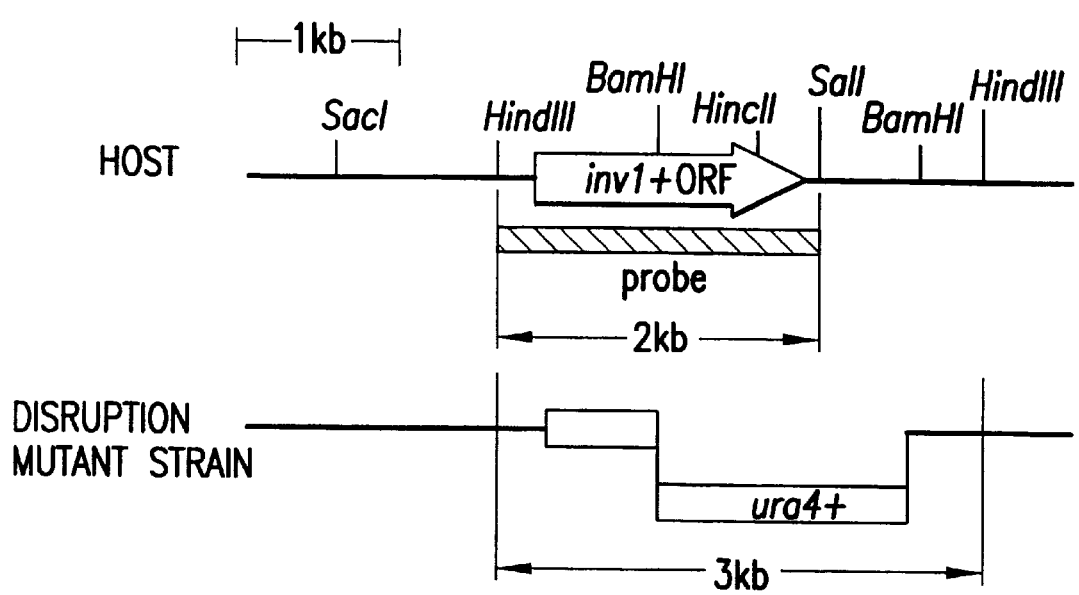
FIG. 2 is the restriction map of the inv1* gene.

Now, the present invention will be described in further detail with reference to specific Examples.

EXAMPLE 1

Isolation of *S. pombe* Invertase Gene

PCR using a *S. pombe* cDNA library as the template and primers designed on the basis of conserved sequences in invertase genes from other organisms shown in SEQ ID NOS: 4 to 6, gave amplification products of about 300 bp and about 400 bp. Each PCR product was purified by using EASY TRAP (Takara Shuzo Co., Ltd.) and sequenced after ligation into a vector by using pMOS Blue T vector kit (Amersham Pharmacia Biotech K.K.). The deduced amino acid sequence indicated that part of the 400-bp PCR product has significant homology with the SUC2 gene from *Saccharomyces cerevisiae*.

Screening of a genomic library of *S. pombe* for the entire invertase gene by plaque hybridization using the 400-bp PCR product as a probe picked up 15 positive clones from about 8,000 plaques. Secondary screening of the positive clones by plaque hybridization left four positive clones. Treatment of small amounts of phage DNA extracts from the positive clones with various restriction enzymes gave identical cleavage patterns, and thus revealed that all the clones were identical.

The entire invertase gene was isolated by the following two-step procedure. A 3.0-kb HindIII fragment was isolated from the hybrid-forming clones and ligated into a plasmid pBluescript II SK– (Toyobo Co., Ltd.). Restriction mapping identified BamHI and SalI sites. Subcloning of the fragment using these restriction enzymes and subsequent sequencing using a deletion technique revealed that the HindIII fragment contains the complete ORF of the gene but contains only about 200 bp within the upstream region, which is supposedly involved in the gene expression. Therefore, separately, a 3.5-kb BamHI fragment from the hybrid-forming clones was further digested with HindIII to give a 2.6-kb fragment. Subcloning of the 2.6-kb fragment in plasmid pBluescript II SK–, and subsequent sequencing using a deletion technique revealed that the BamHi-HindIII fragment contained a sequence within the upstream region supposedly involved in the gene expression. The resulting complete 5.6-kb gene was designated as inv1$^+$. The base sequence of inv1$^+$ and the amino acid sequence encoded by its ORF are shown in SEQ ID NO: 1 and 2. A plasmid carrying the complete gene was designated as pINV3000.

These results suggest that the inv1$^+$ product has 16 asparagine-linked glycosylation sites. FIG. 1 shows a comparison of the amino acid sequence deduced from the base sequence of the inv1$^+$ gene from *S. pombe* (SEQ ID NO: 2), the amino acid sequence of *Schwanniomyces occidentalis* (SEQ ID NO: 23) invertase and the amino acid sequence deduced from the base sequence of the SUC2 gene from *Saccharomyces cerevisiae* (SEQ ID NO: 24). Amino acids that are common to the three are marked with *. FIG. 1 clearly shows the amino acid sequence deduced from the inv1$^+$ base sequence has significant homology with invertases from other origins such as *Schwanniomyces occidentalis* and *Saccharomyces cerevisiae*, which suggests the inv1$^+$ encodes invertase.

EXAMPLE 2

Disruption of the inv1$^+$ Gene

The HindIII site in plasmid pBluescript II SK– having a *S. pombe* ura4$^+$ gene insert at the ClaI site was disrupted by HindIII digestion followed by blunting and self-ligation (self-cyclizaion). Double restriction digestion of the plasmid with XbaI and HincII gave a ura4$^+$ fragment. The plasmid pBluescript was integrated with the ura4$^+$ fragment after restriction digestion with SpeI and subsequent blunting and XbaI digestion, to provide a plasmid having BamHI sites on both sides of ura4$^+$. The BamHI site in plasmid pBluescript II SK– was disrupted similarly by restriction digestion followed by blunting and self-ligation, and the 3.0-kb fragment containing the inv1$^+$ ORF was inserted at the HindIII site. BamHI digestion of the plasmide eliminated a 1.4-kb fragment (containing part of the inv1$^+$ ORF encoding the C-terminal of invertase) from the 3.0-kb insert, and a ura4$^+$ cassette having BamHI sites at both ends was inserted. HindIII digestion of the resulting plasmid gave a DNA fragment having inv1$^+$ neighboring regions at both ends (FIG. 2). The restriction map of the inv1$^+$ gene is shown in FIG. 2, wherein the open reading frame (ORF) is indicated by the arrow (inv1+ORF) and the ura4+ replacement from *Schizosaccharomyces pombe* is boxed (ura4+). The disruption mutant strain had an inv1+ fragment carrying the *S. pombe* ura4+ gene instead of the 1.4-kb inv1+ BamHI-BamHI fragment partly containing the ORF. The inv1+ fragment was used to transform a wild-type *S. pombe* strain, TP4-1D [h−, leu1, ura4, ade6-M216, his2, obtained from Dr. Takashi Toda (Imperial Cancer Research Foundation)], and viable colonies on a uracil-free culture medium were collected. Overlay assay of invertase activity revealed that 7 out of 28 strains, namely 25% of the ura4+ colonies, lacked invertase activity.

Figure 3:
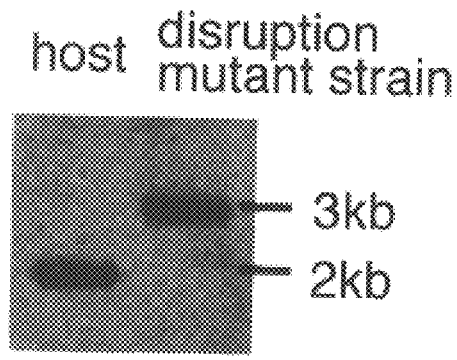
FIG. 3 electrophoretically shows disruption of the inv1* gene.

Further, to verify the chromosomal inv1+ gene disruption, genomic DNA from a strain lacking invertase activity was analyzed after double restriction digestion with HindIII and SalI by Southern hybridization using the inv1+ HindIII-SalI fragment (2 kb) as the probe. The 3-kb hybridized fragment, which was not digested with SalI, shown in FIG. 3 demonstrates that part of the inv1+ gene in the chromosomal DNA had been replaced with the ura4+ gene in the strain which lacked invertase activity.

Thus, the inv1+ gene proved to be the only one invertase gene expressed in *S. pombe*.

EXAMPLE 3

Restoration of Invertase Activity by the inv1+ Gene

The 3.0-kb HindIII fragment containing the entire inv1+ ORF from the invertase gene was inserted into *S. pombe* vector pAU-SK (obtained from Dr. Chikashi Shimoda, Department of Science, Osaka City University), and the resulting recombinant vector was used to transform the invertase-defective strains (Example 2). The resulting transformants were streaked on YP sucrose plates (supplemented with 10 μg/ml antimycin A and 20 μg/ml bromocresol purple) for overlay assay of invertase activity. Further, the 2.6-kb inv1+ BamHI-HindIII fragment containing the upstream promoter region and the 2.0-kb HindIII-SalI fragment from the invertase gene containing the ORF were legated, and the resulting 4.6-kb BamHI-SalI fragment was inserted into pAU-SK. Transformation of the resulting recombinant vector into the invertase-defective strain was followed by similar overlay assay of invertase activity.

Figure 4A:
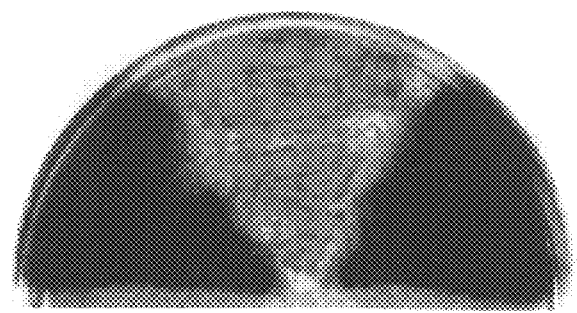
FIGS. 4(a)–4(b).
Figure 4B:
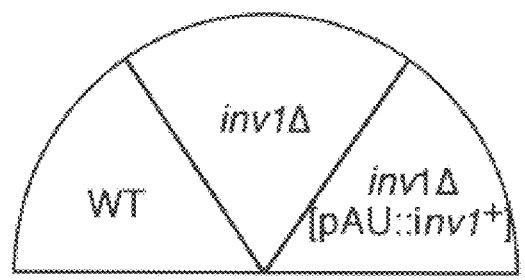

Both transformants (inv1Δ[pAU-SK::inv1+]) and the wild-type strain TP4-1D (WT) developed blue stains, which indicate invertase production, unlike the inv1+ disruption mutant strain (inv1Δ). The addition of the upstream promoter region resulted in stronger stains, which suggest high-level invertase expression (FIGS. 4(a) and 4(b)). FIG. 4(a) is a photograph showing the results of the gel overlay assays, and FIG. 4(b) is a schematic explanation of the stained sections shown in FIG. 4(a).

Figure 5A:
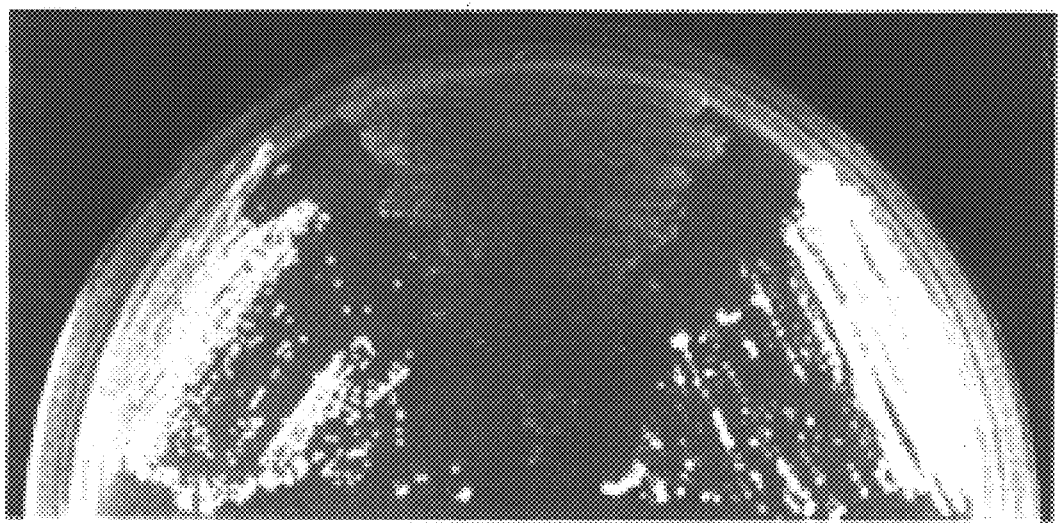
FIGS. 5(a)–5(b).
Figure 5B:
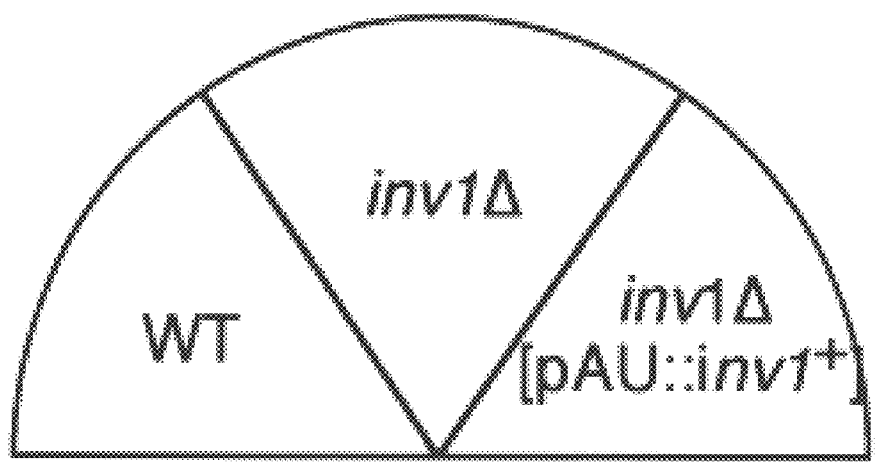

The invertase-defective strain were hardly viable on YP sucrose plates (supplemented with 10 μg/ml antimycin) whereas the wild-type strain and the transformants were recognizably viable after 5 days incubation at 30° C. (FIGS. 5(a) and (b)). FIG. 5(a) is a photograph showing the results of characterization by colony formation, and FIG. 5(b) schematically explains the characterization shown in FIG. 5(a).

These results demonstrate that the inv1+ gene expression product is the invertase located on the cell surface.

EXAMPLE 4

Determination of Glucose Concentration for Gene Repression

Figure 6:
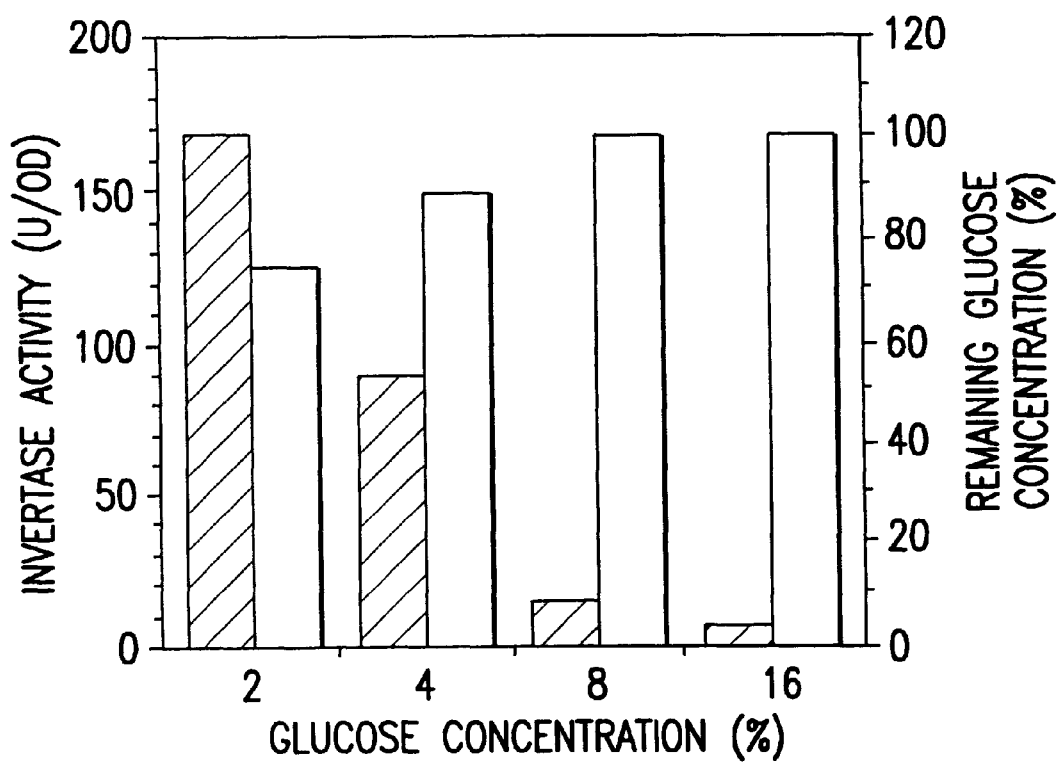
FIG. 6 graphically shows the relation between the invertase activity and the glucose concentration.

For determination of the critical glucose concentration for catabolite repression of the invertase gene, the wild-type strain TP4-1D was incubated at 30° C. in 5 ml of MM medium containing 2%, 4%, 8% and 16% glucose with shaking to the mid-logarithmic growth phase. Invertase assays were done by the method of Goldstein et al., and the post-incubational glucose concentrations in the medium were determined by the phenol-sulfate method (FIG. 6). The hatched bars indicate invertase activity per cell (U/OD), and the empty bars indicate the residual glucose concentration. Judging from the graph, a glucose concentration of 8% is the optimum for glucose repressing incubation, because when the glucose concentration was 8%, the invertase activity was sufficiently repressed with little decrease of glucose.

EXAMPLE 5

Determination of Glucose Concentration for Induced Invertase Production

Figure 7:
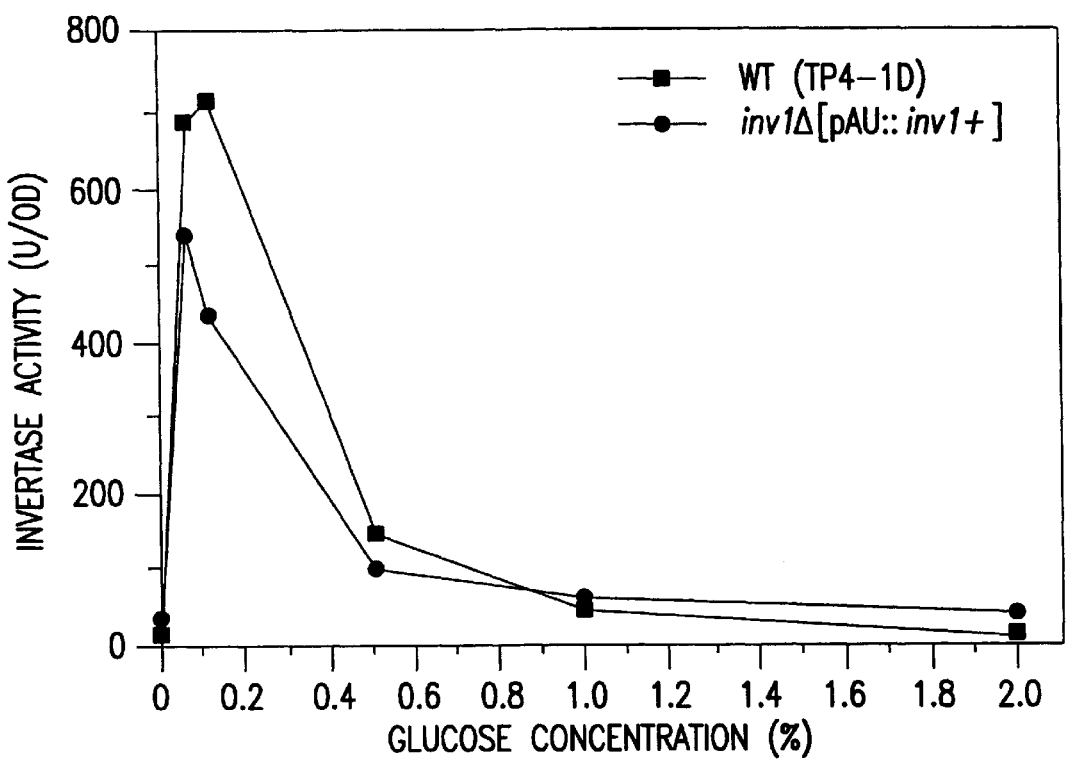
FIG. 7 graphically shows the relation between the invertase activity and the glucose concentration.

For determination of the most effective glucose concentration for induced invertase production, the wild-type strain TP4-1D and a transformant [obtained by transforming the invertase-defective strain (Example 3) with a pAU-SK vector carrying the inv1+ BamHI-SalI fragment] were preincubated in a medium containing 2% glucose to the mid-logarithmic growth phase and incubated in an MM medium containing 0%, 0.01%, 0.05%, 0.1%, 0.25%, 0.5%, 1.0% and 2% glucose with shaking at 27° C. for 3 hours, and the invertase activity was assayed (FIG. 7). Each run of assay was carried out at 30° C. over 180 minutes. 1 U of invertase converts 1 nmol of sucrose into glucose per 1 minute at 30° C., pH 4.0.

The optimum glucose concentration for induction was found to be 0.1% for the wild-type strain and 0.05% for the transformant. The invertase activity in the wild-type strain was 40 times higher under derepressing conditions than under repressing conditions. These results demonstrate catabolite repression in *S. pombe*.

EXAMPLE 6

Analysis of the inv1+ Promoter Region

Fragments obtained ligating *S. pombe* inv1+ upstream sequences extending from positions 1, 620, 1100, 1610 and 2610 of SEQ ID NO: 1, respectively, and the inv1+ ORF were inserted into expression vector pAU-SK to obtain 5 plasmids for deletion studies. The plasmids containing the upstream sequences extending from positions 1, 1610 and 2610 carry the inv1+ BamHI-SalI, SacI-SalI and HindIII-SalI fragments, respectively. The plasmids containing the inv1+ upstream sequences extending from positions 620 and 1100 were constructed by site specific introduction of a SpeI site into pAU-SK::inv1+ (BamHI-SalI) using primers shown in SEQ ID NOS: 7 and 8, respectively, followed by partial removal of the upstream region by SpeI treatment.

Figure 8:
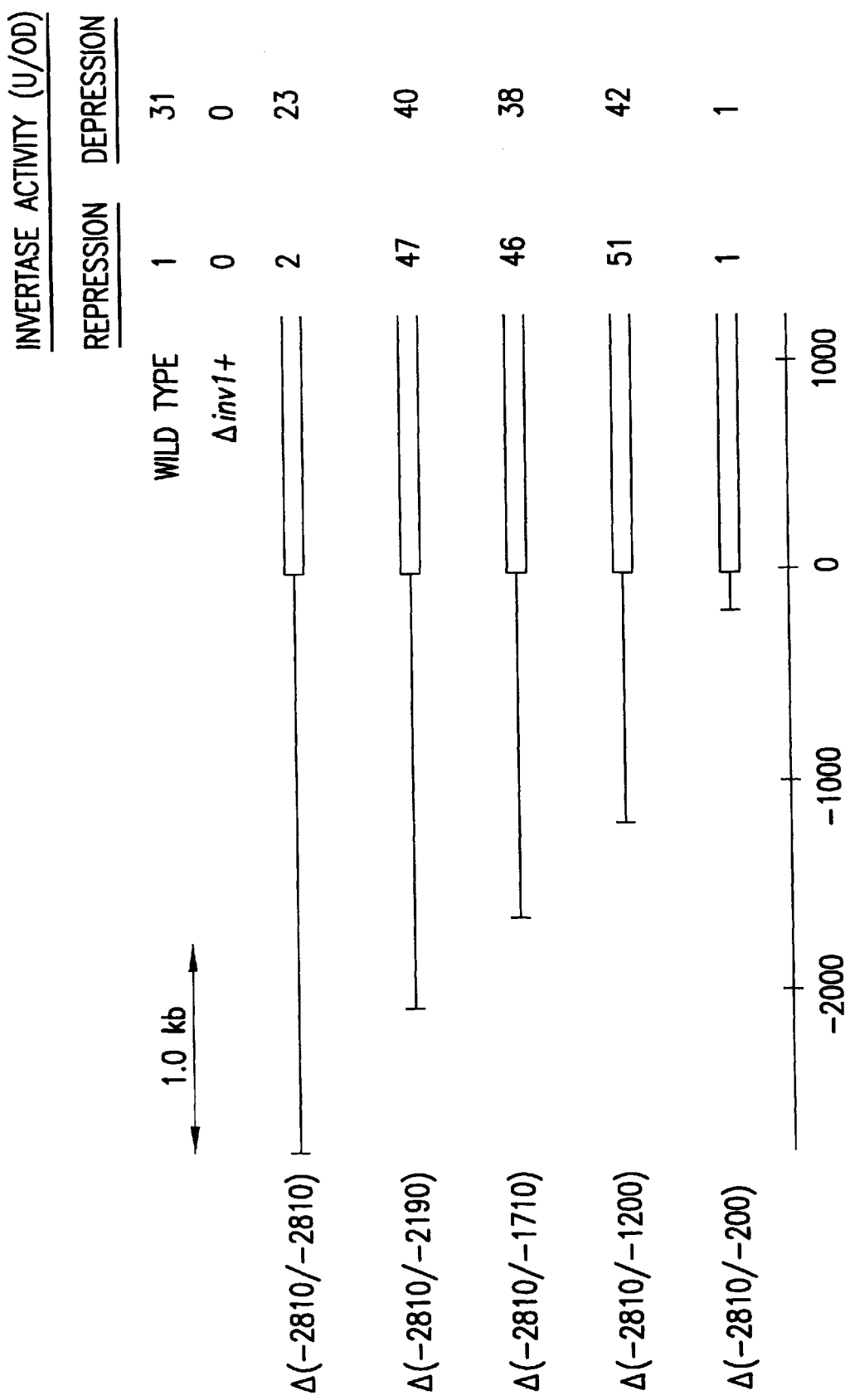
FIG. 8 shows the results of analysis of invertase promoters.

The plasmids thus obtained were used to transform the invertase-defective strain (Example 3). Invertase assays were done to determine the enzyme activity in each transformant (FIG. 8). The results suggest that the sequence between position 1 and position 620 of SEQ ID NO: 1 is essential for glucose repression. The region between position 1620 and position 2610 of SEQ ID NO: 1 was identified as essential for high-level glucose derepression of invertase.

EXAMPLE 7

Construction of Inducible Multicloning Expression Vector pRI0M Carrying the Invertase Promoter PCR amplification using the plasmid pINV3000 (Example 1) carrying the invertase gene from *S. pombe* as the template and oligo DNAs shown in SEQ ID NOS: 9 and 10 as the primers was performed to give a sequence which contains the promoter region for the invertase gene and has restriction enzyme recognition sequences at both ends. After terminal double restriction digestion with SpeI (Takara Shuzo Co., Ltd.) and EcoRI (Takara Shuzo Co., Ltd.), the sequence was subjected to agarose gel electrophoresis. Purification of the band of about 3000 bp by the glass beads method using EASY-TRAP gave an insert fragment.

The S. pombe multicloning vector pTL2M (JP-A-7-163373) was subjected to agarose gel electrophoresis after terminal double restriction digestion with SpeI and EcoI. Purification of the band of about 4500 bp by the glass beads method using EASY-TRAP gave a vector fragment.

Figure 9:
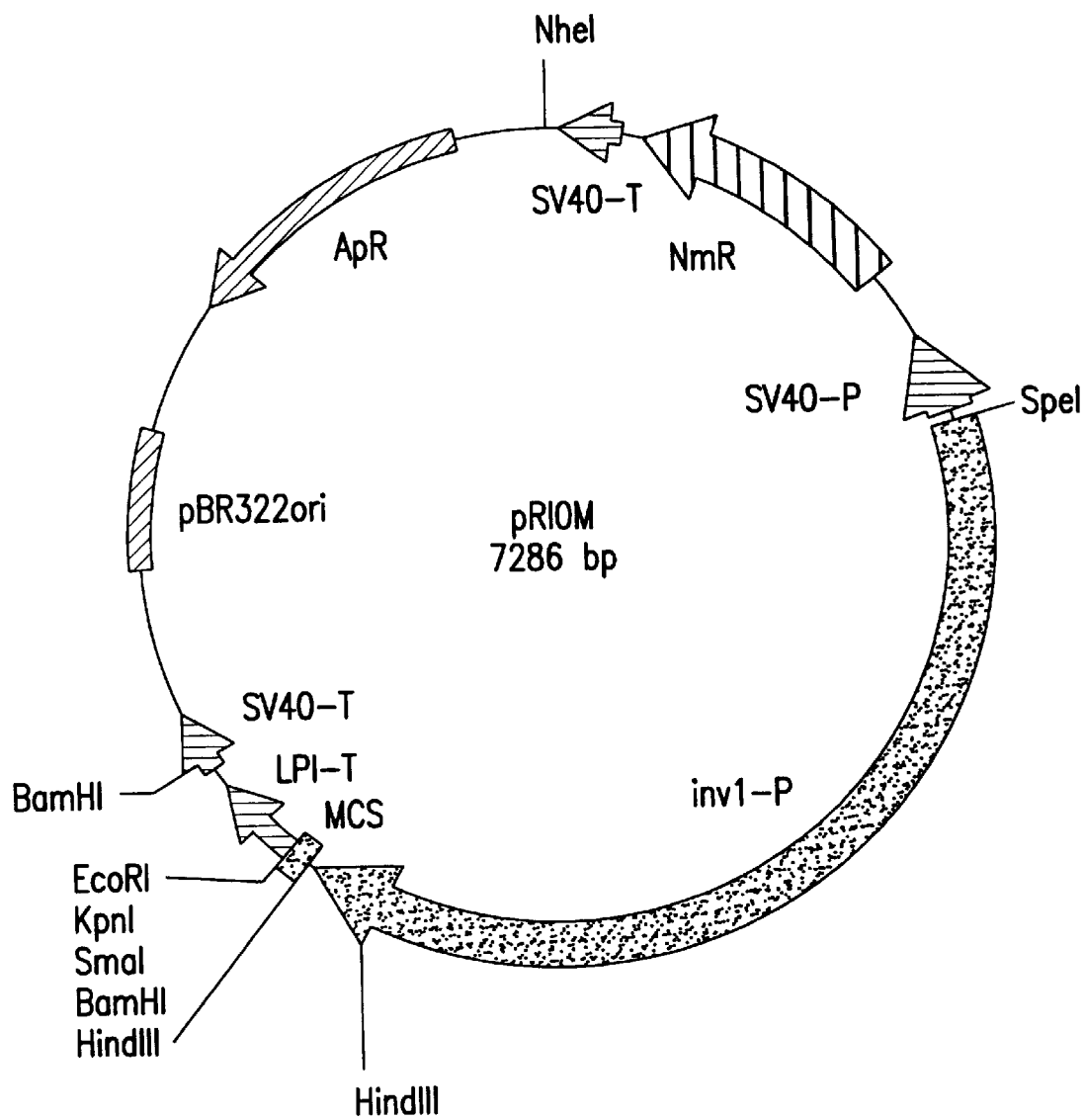
FIG. 9 shows the structure of an inducible expression vector pRI0M.

The two fragments were ligated with a DNA ligation kit (Takara Shuzo Co., Ltd.) and transformed into E. coli strain DH (Toyobo Co., Ltd.). E. coli colonies were screened for the inducible expression vector pRI01M shown in FIG. 9 and SEQ ID NO: 3 in the Sequence Listing through base sequencing and restriction mapping, and the inducible expression vector was recovered by the alkali-SDS method on a preparatory scale.

EXAMPLE 8

Construction of Inducible Expression Vector pRI0EGFP for Expression of Green Fluorescent Protein PCR amplification using the plasmid pINV3000 (Example 1) carrying the invertase gene from S. pombe as the template and oligo DNAs shown in SEQ ID NOS: 9 and 11 as the primers was performed to give a sequence which contains the promoter region for the invertase gene and has restriction enzyme recognition sequences at both ends. After terminal double restriction digestion with SpeI and NheI (Takara Shuzo Co., Ltd.), the sequence was subjected to agarose gel electrophoresis. Purification of the band of about 3000 bp by the glass beads method using EASY-TRAP gave a fragment for use as the promoter insert.

PCR using the plasmid pEGFP carrying the jellyfish (Aequorea victria) green fluorescent protein variant gene (Clontech) as the template and oligo DNAs shown in SEQ ID NOS: 12 and 13 in the Sequence Listing as the primers was performed to amplify the ORF in the green fluorescent protein variant gene. The PCR product was subjected to agarose gel electrophoresis after terminal double restriction digestion with NheI and HindIII. Purification of the band of about 700 bp by the glass beads method using EASY-TRAP gave a fragment for use as the ORF insert.

The S. pombe multicloning vector pTL2M was cleaved by double restriction digestion with SpeI and HindIII and then subjected to agarose gel electrophoresis. Purification of the band of about 4500 bp by the glass beads method using EASY-TRAP gave a vector fragment.

Figure 10:
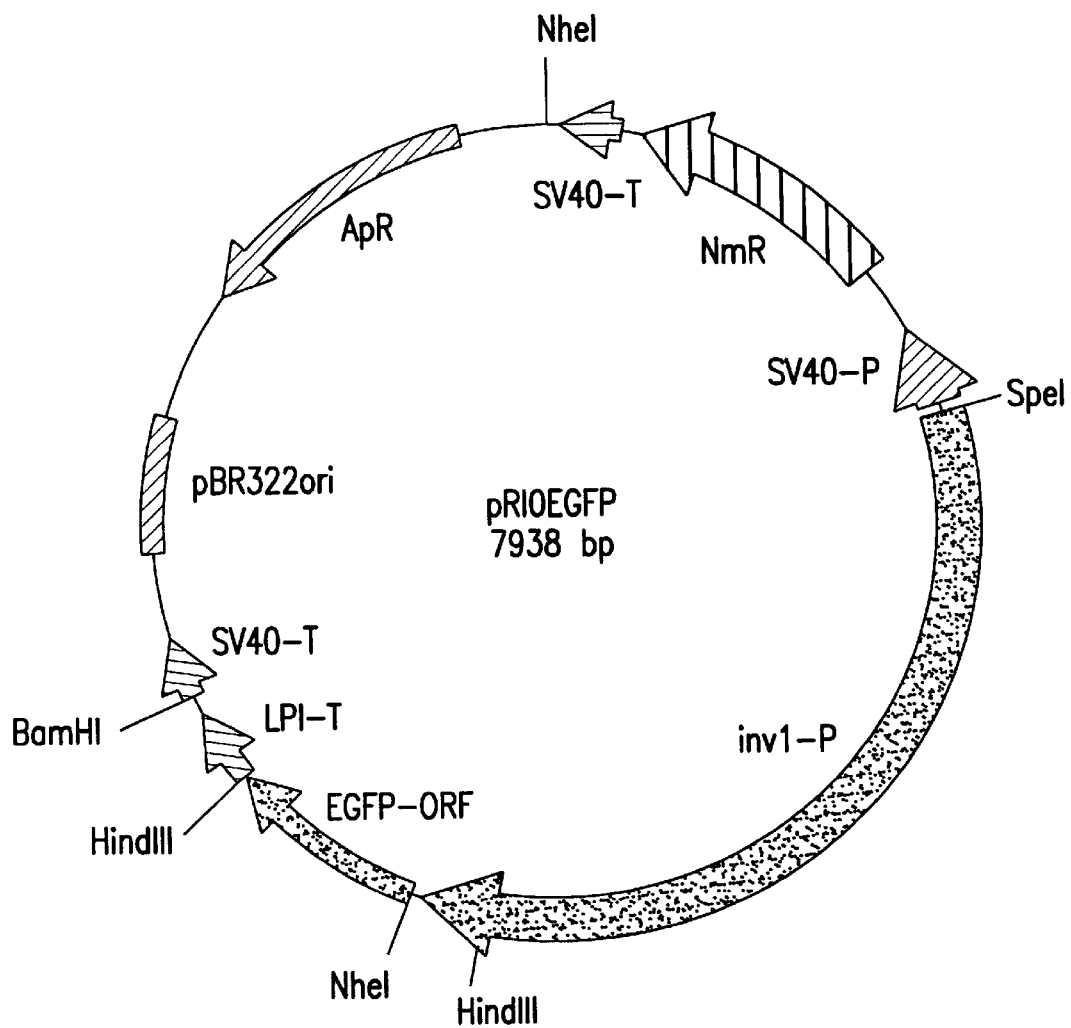
FIG. 10 shows the structure of an inducible expression vector pRI0EGFP for expression of a green fluorescent protein.

The three fragments were ligated with a DNA ligation kit and transformed into E. coli strain DH5. E. coli colonies were screened for the inducible expression vector pRI0EGFP for expression of the green fluorescent protein variant shown in FIG. 10 and SEQ ID NO: 14 in the Sequence Listing through base sequencing and restriction mapping, and the inducible expression vector was recovered by the alkali-SDS method on a preparatory scale.

EXAMPLE 9

Preparation of S. pombe Transformant ASP138

S. pombe wild-type strain ARC001 [leu1-32h⁻ (isogenic to ATCC38399)] was transformed with the inducible expression vector pRI0EGFP for expression of the green fluorescent protein variant and a transducing vector pAL7 as described by Okazaki et al. (Okazaki et al., "Nucleic Acids Res.", 18, 6485–6489, 1990).

1 ml of a preincubated ARC001 culture in YPD medium was incubated in minimum medium MB+Leu with shaking at 30° C. for 14 hours to a cell density of $3 \times 10^7$ per 1 ml, and the cells were collected, washed with water, suspended in 1 ml of 0.1M lithium acetate (pH 5.0) and incubated at 30° C. for 60 minutes. A 100 µl portion of the suspension was mixed with 4 µg of the inducible expression vector pRI0EGFP and 0.5 µg of PstI-digested pAL7 in 15 µl TE and further with 290 µl of 50% PEG 4000 thoroughly and incubated at 30° C. for 60 minutes, at 43° C. for 15 minutes and at room temperature for 10 minutes, successively. After centrifugal removal of PEG, the cells were suspended in 1 ml of ½ YEL+Leu medium. After 10-fold dilution, 1 ml of the suspension was incubated at 32° C. for 2 hours, and a 300 µl portion was spread on minimum medium agar MMA. After 3 days of incubation at 32° C., about 300 independent colonies had developed on the plate.

10 colonies of the transformant were inoculated in 2 ml of YEL medium containing 10 µg/ml antibiotic G418 (YEL10 medium) and incubated with shaking at 32° C. 2 days later, 6 clones were viable. In their subcultures, 4 clones were viable 3 days later. The putative desired transformant (ASP138 strain) was frozen in glycerol and stored for use in subsequent experiments.

EXAMPLE 10

Analysis of Expression of Green Fluorescent Protein Variant

S. pombe transformant ASP138 (Example 9) was inoculated in YPD medium containing 100 µg/ml G418 (YPD100) and incubated at 32° C. for 2 days. Green fluorescence was observed from each cell under a fluorescence microscope (excitation wavelength 490 nm/emission wavelength 530 nm). Green fluorescence emission was also observed upon ultraviolet irradiation from the centrifugally collected cells. Thus, expression of the desired green fluorescent protein in the active form was confirmed.

Strain ASP138 (Example 9) was incubated in 5 ml YPD100 at 32° C. for 3 days, collected, washed and suspended in 50 mM tris-HCl (pH 7.5), disrupted with glass beads in a mini bead beater (Biospec). After removal of the glass beads, the cell extract was heated in the presence of SDS (1%) at 80° C. for 15 minutes. Separately, a negative control was extracted from the transformant carrying pR10M by the same procedure.

Figure 11A:
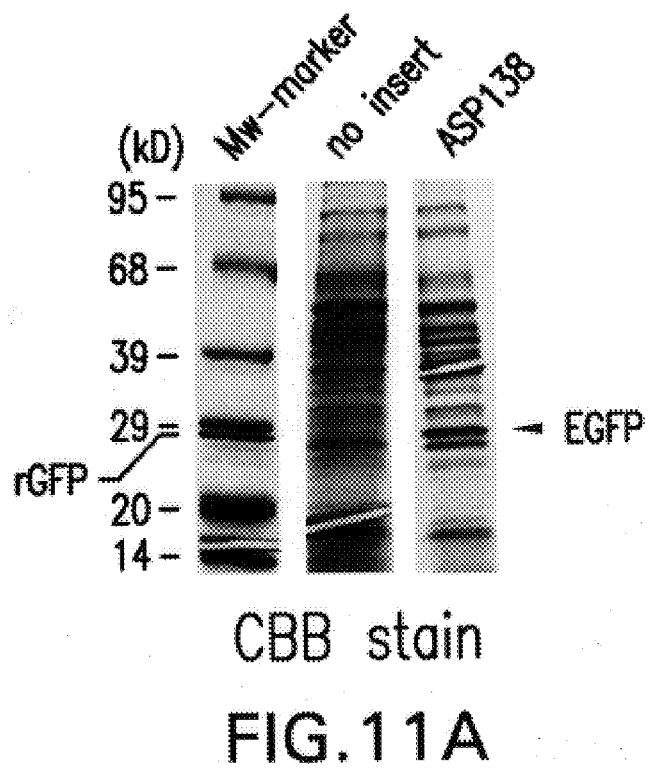
FIGS. 11(a) and 11(b) demonstrate the expression of a green fluorescent protein.
Figure 11B:
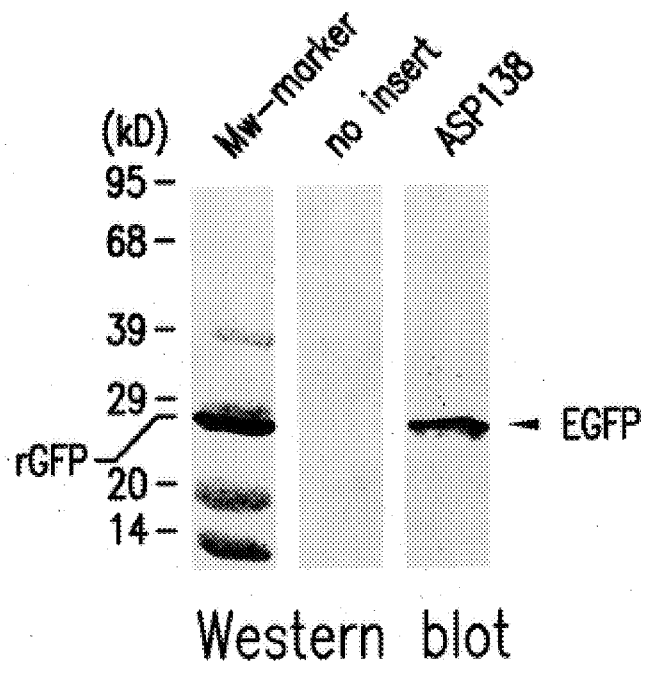

50 µg protein from the extract was analyzed by SDS-polyacrylamide gel electrophoresis (FIGS. 11(a) and (b)). After Coomassie Brilliant Blue (CCB) staining, the extract and a recombinant green fluorescent protein (Clonetech) as the positive control showed major bands with a molecular weight of 25000, but the negative control did not. Further, 50 µg protein from the extract was analyzed by SDS-polyacrylamide gel electrophoresis followed by western blotting on a PVDF membrane using an anti-green fluorescent protein antibody (Clonetech). The cell extract and the positive control showed major bands with a molecular weight of 25000, but the negative control did not. These results provide biological evidence of expression of the desired green fluorescent protein.

EXMAPLE 11

Optimization of the Incubation Method (1)

The transformed S. pombe strain ASP (Example 9) was incubated in YPD medium containing 100 µg/ml G418

Figure 12A:
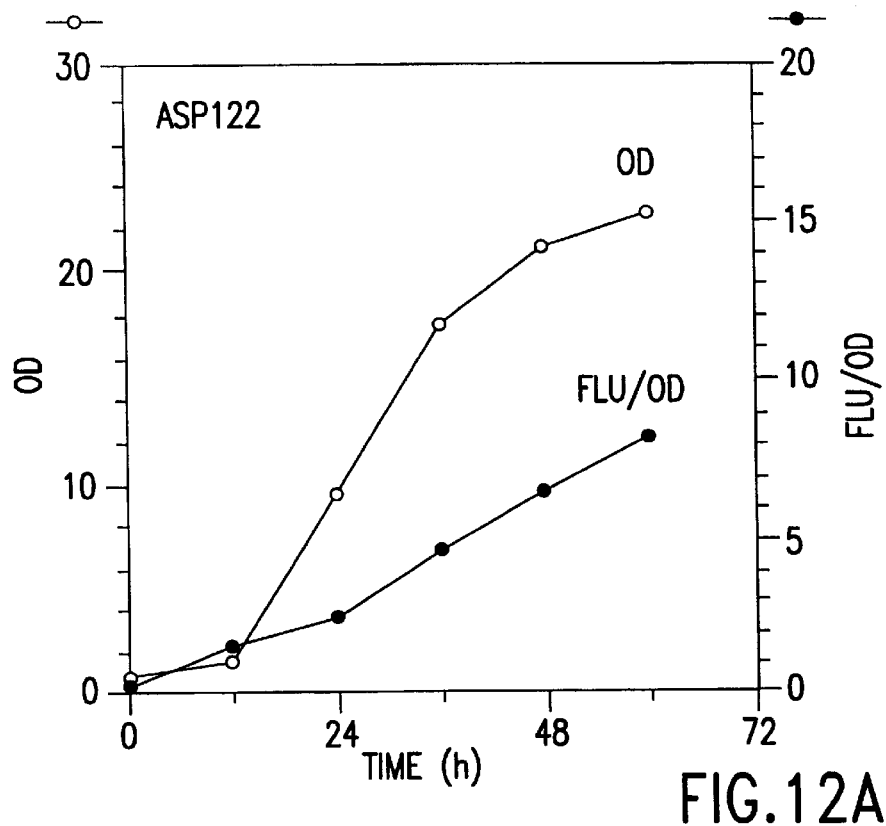
FIGS. 12(a) and 12(b) graphically show the relation between the incubation time and the expression level of the green fluorescent protein.
Figure 12B:
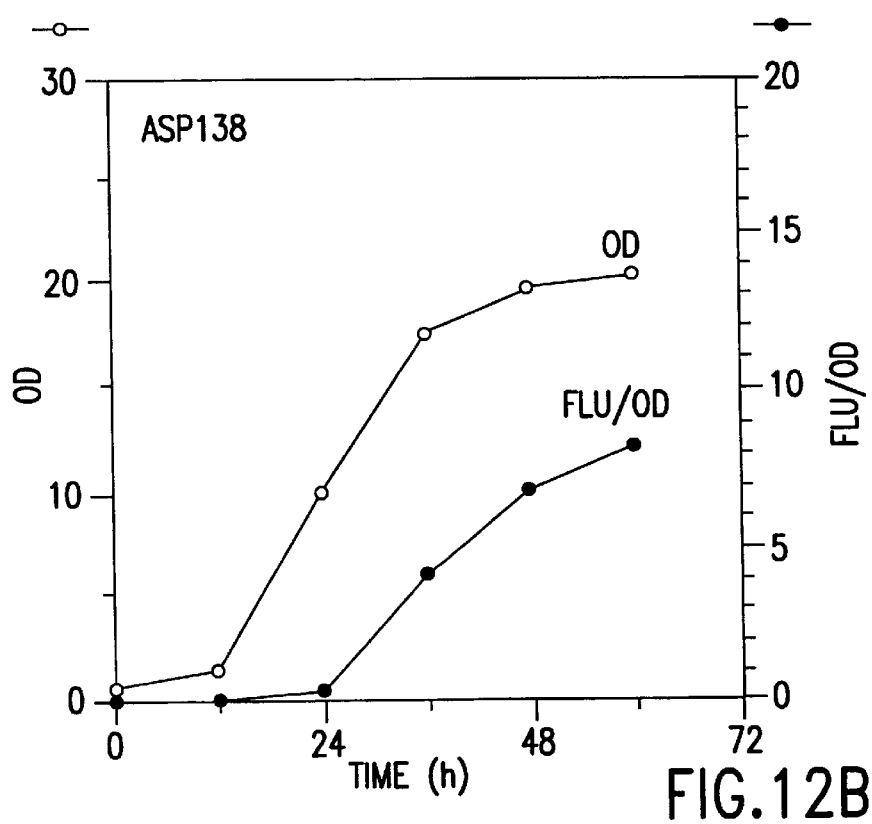

(YPD100) at 32° C. The expression level of the green fluorescent protein in the cell culture was determined fluorometrically by means of a microplate reader (Corona Electric Co., Ltd.) equipped with a fluorescent attachment (excitation wavelength 490 nm/emission wavelength 530 nm) (FIGS. 12(a) and (b)). OD, FLU/OD and time denote the cell density, the fluorescence intensity per cell and the incubation time, respectively. The results show that strain ASP138 did not express the green fluorescent protein variant until the late-growth phase after glucose exhaustion in the mid-growth phase, unlike strain ASP122 having a non-inducible cytomegalovirus promoter [a transformant carrying a recombination product of phGFPS65T (Clonetech) for expression of a green fluorescent protein variant of S65T prepared as disclosed in JP-A-7-163373], clearly due to repression of the inducible invertase promoter in the presence of glucose and subsequent derepression by glucose exhaustion, demonstrating the applicability of this mechanism to expression of the green fluorescent protein as a heterologous protein.

EXAMPLE 12

Incubation of Strain ASP138 (2)

Figure 13A:
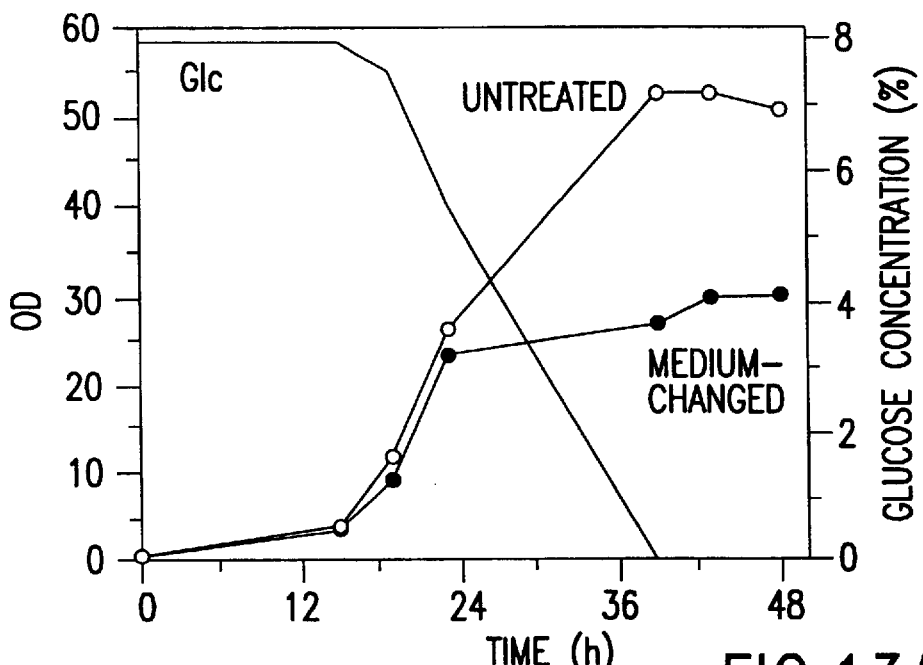
FIGS. 13(a) and 13(b) graphically show the relation between the incubation time and the expression level of the green fluorescent protein.
Figure 13B:
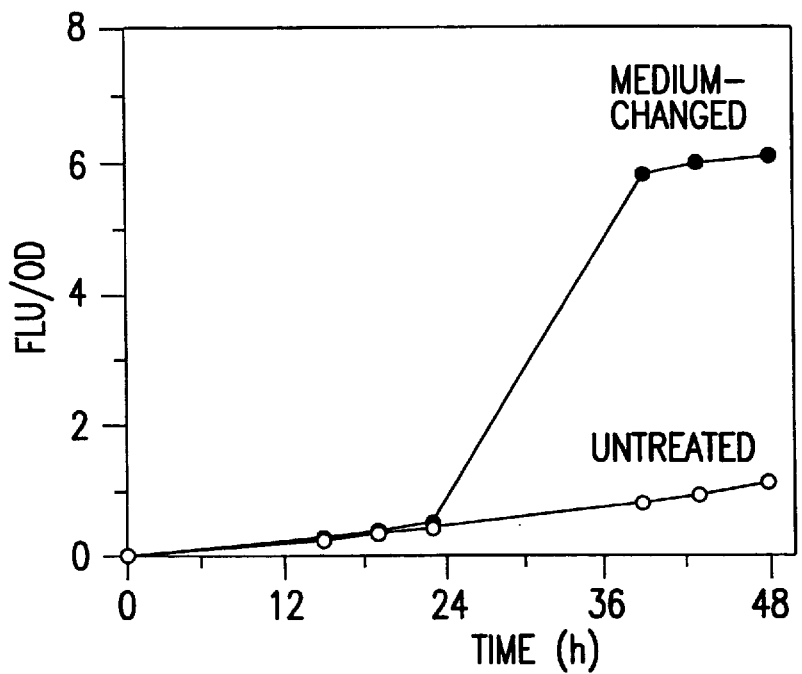

The transformed *S. pombe* strain ASP138 (Example 9) was incubated in YPD medium containing 100 μg/ml G418 (glucose concentration 8%) at 32° C. to the mid-growth phase, and after medium change, incubated in YPDG medium containing 100 μg/ml G418 (glucose concentration 0.1%, glycerol concentration 3%) (FIGS. 13(a) and (b)). OD, FLU/OD and time denote the cell density, the fluorescence intensity per cell and the incubation time, respectively. The results show that while the green fluorescent protein was not expressed in the cells incubated without medium change (Untreated), expression of the green fluorescent protein in the cells incubated with the medium change was activated by the medium change (Medium-changed) probably because the depletion of glucose in the medium provoked derepression of the invertase promoter and thereby induced the protein expression. The high level expression induced by the medium change to a low-glucose expression medium suggests that use of a growth medium (with a high glucose concentration) and an expression medium (with a low glucose concentration) can differentiate between cell growth and protein expression. It was demonstrated that the repression of the inducible invertase promoter in the presence of glucose and derepression by exhaustion of glucose could be utilized in expression of the green fluorescent protein as a heterologous protein.

EXAMPLE 13

Incubation of Strain ASP138 (3)

Figure 14A:
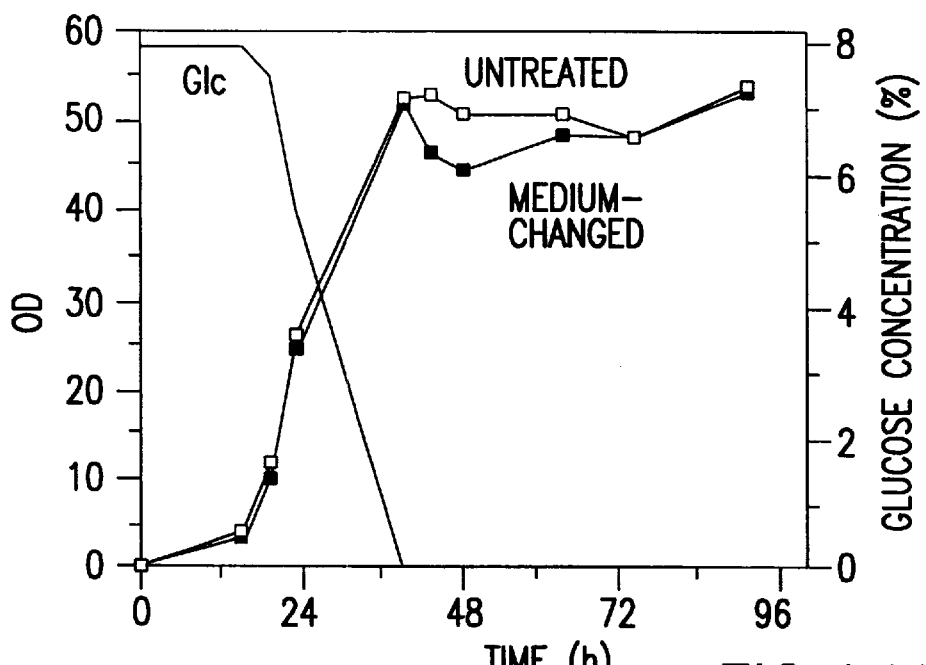
FIGS. 14(a) and 14(b) show the relation between the incubation time and the expression level of the green fluorescent protein.
Figure 14B:
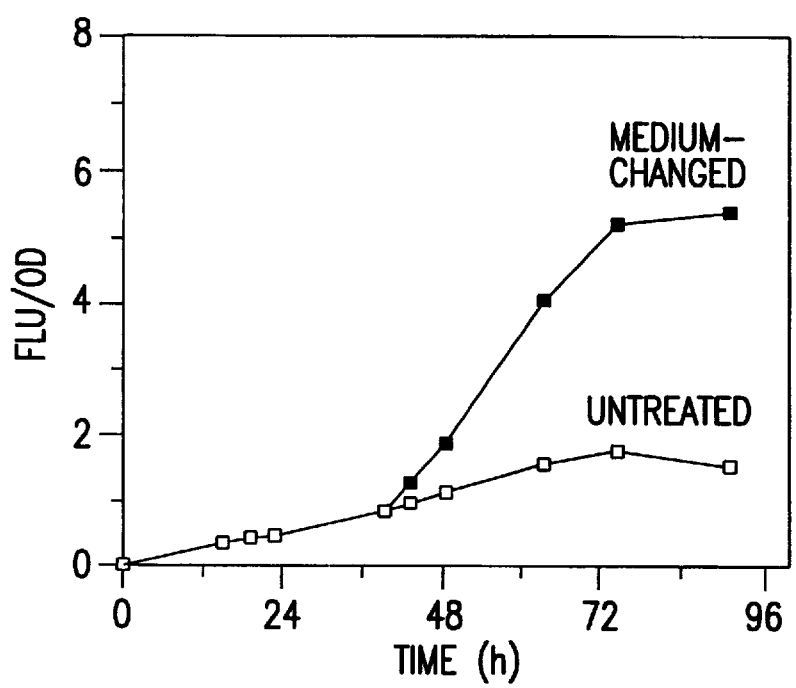

The transformed *S. pombe* strain ASP138 (Example 9) was incubated in YPD medium containing 100 μg/ml G418 (glucose concentration 8%) at 32° C. to the late-growth phase, and after medium change, incubated in YPDG medium containing 100 μg/ml G418 (glucose concentration 0.1%, glycerol concentration 3%) (FIGS. 14(a) and (b)). OD, FLU/OD and time denote the cell density, the fluorescence intensity per cell and the incubation time, respectively. The results show that while the green fluorescent protein was not expressed in the cells incubated without medium change (Untreated), expression of the green fluorescent protein in the cells incubated with the medium change was activated by the medium change (Medium-changed) probably because the depletion of glucose in the medium provoked derepression of the invertase promoter and thereby induced the protein expression. The high level expression induced by the medium change to a low-glucose expression medium from a high-glucose medium before glucose exhaustion suggests that use of a growth medium (with a high glucose concentration) and an expression medium (with a low glucose concentration) can differentiate between cell growth and protein expression. It was demonstrated that the repression of the inducible invertase promoter in the presence of glucose and derepression by exhaustion of glucose could be utilized in expression of the green fluorescent protein as a heterologous protein.

EXAMPLE 14

Construction of Inducible Lipocortin I Expression Vector pRI0LPI

PCR using plasmid pINV3000 (Example 1) carrying the *S. pombe* invertase gene as the template and oligo DNAs shown in SEQ ID NOS: 15 and 16 in the Sequence Listing as primers gave an amplification product containing the promoter region in the invertase gene and having restriction enzyme recognition sequences at both ends. After terminal double restriction digestion with SpeI and EcoRI, the amplification product was subjected to agarose gel electrophoresis. Purification of the band of about 3000 bp by the glass beads method using EASY-TRAP gave a fragment for use as a promoter insert.

The expression vector pTL2L (JP-A-7-163373) carrying a human lipocortin I gene was subjected to agarose gel electrophoresis after terminal double restriction digestion with EcoRI and HindIII. Purification of the band of about 1000 bp by the glass beads method using EASY-TRAP gave a fragment for use as the OPF insert.

The *S. pombe* multicloning vector pTL2M (JP-A-7-163373) was subjected to agarose gel electrophoresis after terminal double restriction digestion with SpeI and HindIII. Purification of the band of about 4500 bp by the glass beads method using EASY-TRAP gave a vector fragment.

The three fragments were ligated with a DNA ligation kit and transformed into *E. coli* strain DH5. *E. coli* colonies were screened for the inducible lipocortin I expression vector pRI0LPI through base sequencing and restriction mapping, and the vector was recovered by the alkali-SDS method on a preparatory scale.

EXAMPLE 15

Preparation of Fission Yeast *Schizosaccharomyces pombe* Transformant ASP139

A *S. pombe* wild-type strain ARC001 was transformed with the inducible lipocortin I expression vector pRI0LPI and a transducing vector pAL7 as described by Okazaki et al.

1 ml of a preincubated ARC001 culture in YPD medium was incubated in minimum medium MB+Leu with shaking at 30° C. for 16 hours to a cell density of $1 \times 10^7$ per 1 ml, and the cells were collected, washed with water, suspended in 1 ml of 0.1M lithium acetate (pH 5.0) and incubated at 30° C. for 60 minutes. A 100 μl portion of the suspension was mixed with 2 μg of the recombinant vector pRI0LPI and 0.5 μg of PstI-digested pAL7 in 15 μl TE and further with 290 μl of 50% PEG 4000 thoroughly and incubated at 30° C. for 60 minutes, at 43° C. for 15 minutes and at room temperature for 10 minutes, successively. After centrifugal removal of PEG, the cells were suspended in 1 ml of ½ YEL+Leu medium. After 10-fold dilution, 1 ml of the suspension was incubated at 32° C. for 2 hours, and a 300 μl portion was spread on minimum medium agar MMA. After 3 days of incubation at 32° C., about 300 independent colonies had developed on the plate.

10 colonies of the transformant were inoculated in 2 ml of YEL medium containing 10 μg/ml antibiotic G418 (YEL10 medium) and incubated with shaking at 32° C. 2 days later, 2 clones were viable. All the subcultures of them were viable 3 days later. The putative desired transformant (ASP138 strain) was frozen in glycerol and stored for use in subsequent experiments.

EXAMPLE 16

Analysis of Lipocortin I Expression

S. pombe transformant ASP139 (Example 15) was incubated in YPD medium containing 100 μg/ml G418 (glucose concentration 8%) at 32° C. to the stationary phase and collected as a non-inducible cell culture. Separately, ASP139 was incubated in the same medium at first to the mid-growth phase, then after medium change, incubated in YPDG medium containing 100 μg/ml G418 (glucose concentration 0.1%, glycerol concentration 3%) to the stationary phase and collected as an inducible cell culture. Both cell cultures were washed, suspended in 50 mM tris-HCl (pH 7.5) and disrupted with glass beads in a mini bead beater. After removal of the glass beads, the cell extracts were heated in the presence of SDS (1%) at 80° C. for 15 minutes.

50 μg protein from each extract was separated by SDS-polyacrylamide gel electrophoresis and stained with Coomassie Brilliant Blue. The extract from the inducible cell culture showed a major band of a molecular weight of about 45000, which is the same as the deduced molecular weigh of the recombinant lipocortin I protein, but the extract from the non-inducible cell culture did not. More sensitive western analysis of band density showed that the band from the inducible cell culture extract was 10 times denser than the band from the non-inducible cell culture extract. The results show that while lipocortin I was not expressed in the cells incubated without medium change, the expression of lipocortin I in the cells incubated with the medium-change was activated by the medium change probably because the depletion of glucose in the medium provoked derepression of the invertase promoter and thereby induced the protein expression. The high level expression induced by the medium change to a low-glucose expression medium from a high-glucose medium suggests that use of a growth medium (with a high glucose concentration) and an expression medium (with a low glucose concentration) can differentiate between cell growth and protein expression. It was demonstrated that the repression of the inducible invertase promoter in the presence of glucose and derepression by exhaustion of glucose could be utilized in expression of lipocortin I as a heterologous protein.

EXAMPLE 17

Construction of Expression Vector pTL2INV1 Carrying Invertase Gene

PCR using plasmid pINV3000 (Example 1) carrying the S. pombe invertase gene as the template and oligo DNAs shown in SEQ ID NOS: 17 and 18 in the Sequence Listing as primers gave an amplification product containing the ORF in the invertase gene and having restriction enzyme recognition sequences at both ends. After terminal double restriction digestion with AflIII (New England Biolab) and HindIII (Takara Shuzo Co., Ltd), the amplification product was subjected to agarose gel electrophoresis. Purification of the band of about 3000 bp by the glass beads method using EASY-TRAP gave a fragment for use as an insert.

The S. pombe multicloning vector pTL2M (JP-A-7-163373) was subjected to agarose gel electrophoresis after terminal double restriction digestion with SpeI and EcoI. Purification of the band of about 4500 bp by the glass beads method using EASY-TRAP gave a vector fragment.

The two fragments were ligated with a DNA ligation kit (Takara Shuzo Co., Ltd) and transformed into E. coli strain DH5 (Toyobo Co., Ltd.). E. coli colonies were screened for the invertase gene expression vector pRI0LPI through base sequencing and restriction mapping, and the vector was recovered multiplied by the alkali-SDS method on a preparatory scale.

EXAMPLE 18

Construction of Secretory Expression Vector pSL2I06a'c1 Using the Signal Sequence from the Invertase Gene PCR using plasmid pINV3000 (Example 1) carrying the S. pombe invertase gene as the template and oligo DNAs shown in SEQ ID NOS: 19 and 20 in the Sequence Listing as primers gave an amplification product containing the ORF in the invertase gene and having restriction enzyme recognition sequences at both ends. After terminal double restriction digestion with SpeI (Takara Shuzo Co., Ltd.) and EcoRI (Takara Shuzo Co., Ltd.), the amplification product was subjected to agarose gel electrophoresis. Purification of the band of about 700 bp by the glass beads method using EASY-TRAP (Takara Shuzo Co., Ltd.) gave a fragment for use as a signal insert.

PCR using plasmid pSL2P06a'c1 (WO96/23890) containing human iterleukin 6a'c1 variant cDNA as the template and oligo DNAs shown in SEQ ID NOS: 21 and 22 in the Sequence Listing as primers gave an amplification product containing the iterleukin 6a'c1 variant ORF. After terminal double restriction digestion with EcoRI and HindIII (Takara Shuzo Co., Ltd), the amplification product was subjected to agarose gel electrophoresis. Purification of the band of about 600 bp by the glass beads method using EASY-TRAP (Takara Shuzo Co., Ltd.) gave a fragment for use as a gene insert.

The S. pombe multicloning vector pTL2M (JP-A-7-163373) was subjected to agarose gel electrophoresis after terminal double restriction digestion with SpeI and HindIII. Purification of the band of about 4500 bp by the glass beads method using EASY-TRAP gave a vector fragment.

The three fragments were ligated with a DNA ligation kit and transformed intothe E. coli strain DH5 (Toyobo Co., Ltd.). E. coli colonies were screened for the IL-6a'c1 secretory expression vector pSL2I06a'c1 through base sequencing and restriction mapping, and the vector was recovered by the alkali-SDS method on a preparatory scale.

EXAMPLE 19

Preparation of S. pombe Transformant ASP168

A leucine-requiring S. pombe strain ARC001 was transformed with the interleukin-6a'c1 variant secretory expression vector pSL2I06a'c1 (Example 18) and a transducing vector pAL7 as described by Okazaki et al.

1 ml of a preincubated ARC001 culture in YPD medium was incubated in 100 minimum medium MB+Leu with shaking at 30° C. for 16 hours. The cells were collected, washed with water, suspended in 0.1M lithium acetate (pH 5.0) at a cell density of $10^9$ cells/ml and incubated at 30° C. for 60 minutes. A 100 µl portion of the suspension was mixed with 2 µg of the recombinant vector pSL2I06a'c1 and 1.0 µg of PstI-digested pAL7 in 15 µl TE and further with 290 µl of 50% PEG 4000 thoroughly and incubated at 30° C. for 60 minutes, at 43° C. for 15 minutes and at room temperature for 10 minutes, successively. After centrifugal removal of PEG, the cells were suspended in 1 ml of ½ YEL+Leu medium. After 10-fold dilution, 1 ml of the suspension was incubated at 32° C. for 2 hours, and a 300 µl portion was spread on minimum medium agar MMA. After 3 days of incubation at 32° C., about 1000 independent colonies had developed on the plate.

The transformants (colonies) were inoculated in 2 ml of YEL medium containing 10 µg/ml antibiotic G418 (YEL10 medium) and incubated with shaking at 32° C. for 5 days. The viable clones of the putative desired transformant, designated as strain ASP168, were frozen in glycerol and stored for use in subsequent experiments.

EXAMPLE 20

Analysis of Expressed Secretory Interleukin-6a'c1 Variant in Culture Medium A fission yeast *Schizosaccharomyces pombe* transformant ASP168 (Example 19) was incubated in MA-Casamino acid medium (MA medium containing 2% Casamino acid and 3% glucose; for the composition of MA medium, refer to "Alfa et al., Experiments with Fission Yeast, Cold Spring Harbor Laboratory Press, 1993") containing 500 µg/ml G418 at 32° C. for 2 days.

Figure 15:
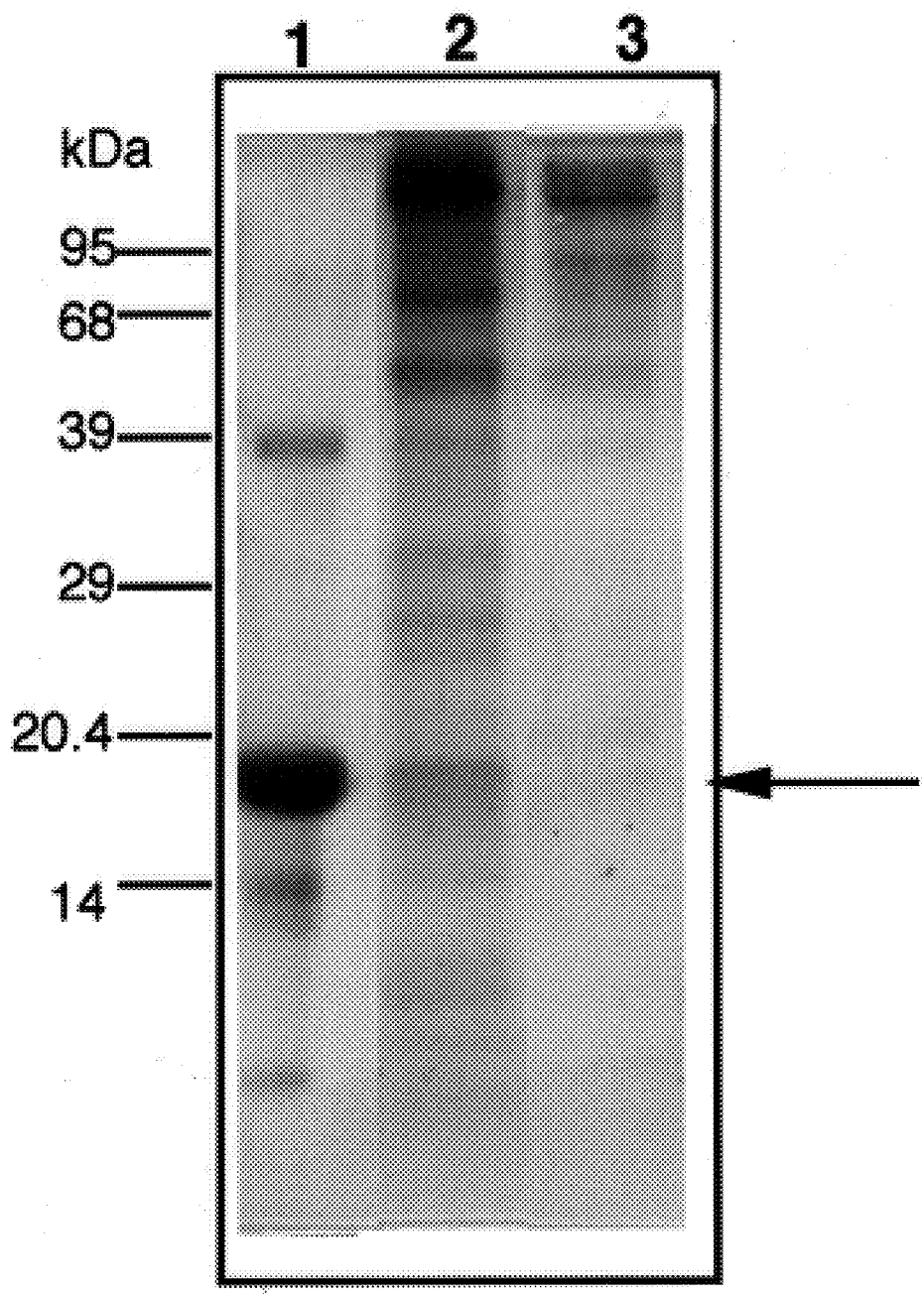
FIG. 15 is a SDS-PAGE pattern obtained in analysis of the expression of interleukin 6a'c1 variant.

The cell culture was centrifuged, and the supernatant was concentrated 100-fold through a membrane filter (Amicon Co., Ltd.). Analysis of the concentrated sample by SDS-polyacrylamide electrophoresis followed by Coomassie Brilliant Blue staining gave the SDS-PAGE pattern shown in FIG. 15. Lane 1 is the purified interleukin-6a'c1 variant, lane 2 is the supernatant from the ASP168 cell culture, and lane 3 is the supernatant from a cell culture of the control strain ASP021 [transformant carrying a recombinant vector with no ORF prepared by recombination of pTL2M (JP-A-7-163373) by the method disclosed in JP-A-7-163373 without introduction of any gene to be expressed]. The band with a molecular weight of about 20000 in lane 3 seemed attributable to the interleukin-6a'c1 variant from the comparison of lanes 1 and 3.

Figure 16:
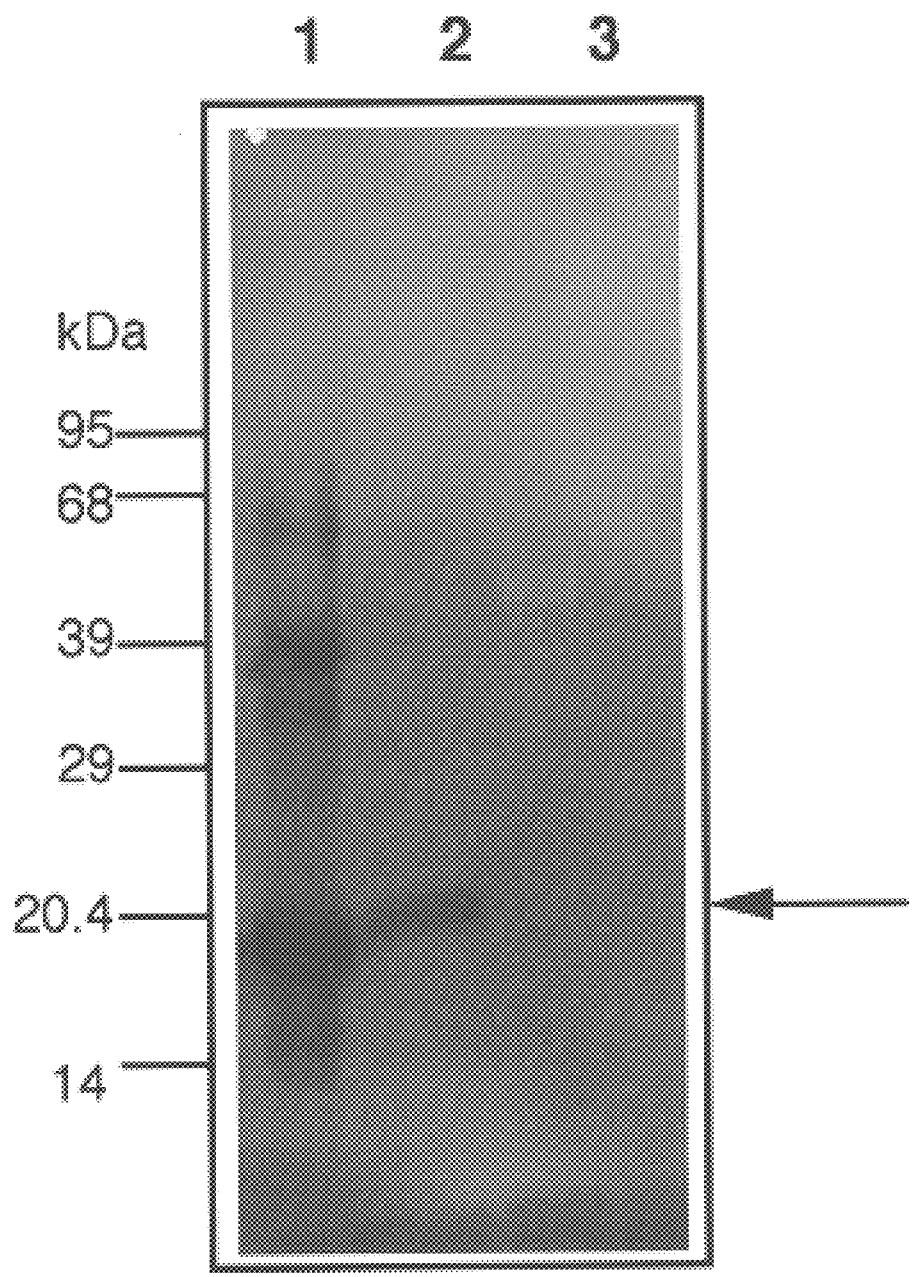
FIG. 16 is the western blot pattern of the expressed interleukin variant.

Further analysis by western blotting using an anti-IL-6a'c1 gave the pattern shown in FIG. 16. Lane 1 is the purified interleukin-6a'c1 variant, lane 2 is the supernatant from the ASP168 cell culture, and lane 3 is the supernatant from a cell culture of the control strain ASP021. The band with a molecular weight of about 20000 in lane 3 was identified as the interleukin-6a'c1 variant from the comparison of lanes 1 and 3.

What is claimed is:

1. An isolated DNA having the base sequence of bases 1 to 2809 in SEQ ID NO: 1 in the Sequence Listing.

2. An isolated DNA encoding a polypeptide consisting essentially of amino acids 1–22 of SEQ ID NO: 2.

3. A recombinant vector containing the sequence of the DNA according to claim 1 or 2.

4. A cloning vector containing the sequence of the DNA according to claim 1 or 2 and a multicloning site.

5. A cloning vector having the structure shown in FIG. 9.

6. An expression vector containing the sequence of the DNA according to claim 1 or 2 and a heterologous protein structural gene.

7. A *Schizosaccharomyces pombe* transformant carrying the expression vector according to claim 6.

8. A process for producing a protein which comprises incubating the transformant according to claim 7 and recovering an expressed heterologous protein.

9. The DNA of claim 2, wherein the polypeptide consists of amino acids 1–22 of SEQ ID NO: 2.

10. An expression vector containing the DNA of claim 9 and a heterologous protein structural gene.

11. A *Schizosaccharomyces pombe* transformant carrying the expression vector of claim 10.

12. A method of producing a protein, comprising incubating the transformant of claim 11 and recovering an expressed heterologous protein.

* * * * *